(12) United States Patent
Pisarnwongs et al.

(10) Patent No.: US 9,474,544 B2
(45) Date of Patent: Oct. 25, 2016

(54) METHOD AND APPARATUS FOR ACCESSING THE INTERIOR OF A HIP JOINT, INCLUDING THE PROVISION AND USE OF A NOVEL INFLOW ACCESS CANNULA

(75) Inventors: Roger Pisarnwongs, Valencia, CA (US); Jolene Cutts, San Francisco, CA (US)

(73) Assignee: Pivot Medical, Inc., Sunnyvale, CA (US)

( * ) Notice: Subject to any disclaimer, the term of this patent is extended or adjusted under 35 U.S.C. 154(b) by 1072 days.

(21) Appl. No.: 13/177,446

(22) Filed: Jul. 6, 2011

(65) Prior Publication Data

US 2012/0010670 A1 Jan. 12, 2012

Related U.S. Application Data

(60) Provisional application No. 61/361,783, filed on Jul. 6, 2010.

(51) Int. Cl.
*A61F 2/46* (2006.01)
*A61B 17/34* (2006.01)
*A61B 17/17* (2006.01)

(52) U.S. Cl.
CPC ........ *A61B 17/3421* (2013.01); *A61B 17/1746* (2013.01); *A61B 17/3496* (2013.01); *A61B 2017/3454* (2013.01); *A61B 2017/3456* (2013.01); *A61B 2217/005* (2013.01); *A61B 2217/007* (2013.01)

(58) Field of Classification Search
CPC .................. A61B 17/3421; A61B 2017/3454; A61B 2217/005; A61B 2217/007; A61B 17/1746; A61B 17/3496

USPC ........................ 604/167.01–167.04, 26, 264; 600/121–125, 201–249; 606/108, 129, 606/184, 185
See application file for complete search history.

(56) References Cited

U.S. PATENT DOCUMENTS

| | | | |
|---|---|---|---|
| 5,312,351 A | 5/1994 | Gerrone | |
| 5,318,585 A | 6/1994 | Guy et al. | |
| 5,347,988 A | 9/1994 | Hori | |
| 5,368,014 A | 11/1994 | Anapliotis et al. | |
| 5,456,673 A * | 10/1995 | Ziegler et al. | 604/264 |
| 6,450,992 B1 * | 9/2002 | Cassidy, Jr. | 604/164.01 |
| 8,425,532 B2 | 4/2013 | Flom et al. | |
| 2002/0010425 A1 * | 1/2002 | Guo et al. | 604/167.04 |
| 2003/0009175 A1 * | 1/2003 | Cassidy, Jr. | 606/108 |
| 2005/0010238 A1 * | 1/2005 | Potter et al. | 606/129 |
| 2007/0088277 A1 * | 4/2007 | McGinley et al. | 604/167.01 |
| 2009/0192466 A1 * | 7/2009 | Sniffin | 604/167.01 |
| 2011/0087169 A1 * | 4/2011 | Parihar | A61B 17/34 604/167.03 |

* cited by examiner

*Primary Examiner* — Matthew Lawson
(74) *Attorney, Agent, or Firm* — Pandiscio & Pandiscio

(57) ABSTRACT

An inflow access cannula system for allowing an instrument to access a surgical site, the system including an inflow access cannula including distal and proximal ends and a central lumen extending therebetween, and an instrument adapter for releasable connection to the cannula, the adapter including a lumen communicating with the central lumen, the adapter further including a port and a fluid passageway connecting the port with the lumen of the adapter, and a spacer for spacing the proximal portion of the instrument from the distal end of the cannula, such that when the distal portion of an instrument extends within the central lumen and the proximal portion of the instrument is disposed in the lumen, in engagement with the spacer, fluid can flow into the port, along the fluid passageway, into the lumen and through the central lumen.

13 Claims, 31 Drawing Sheets

CAM-TYPE FEMOROACETABULAR IMPINGEMENT (FAI)
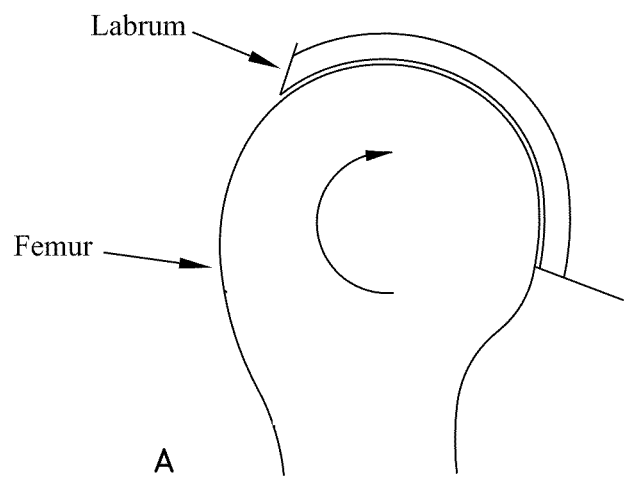
CAM INJURY TO THE LABRUM
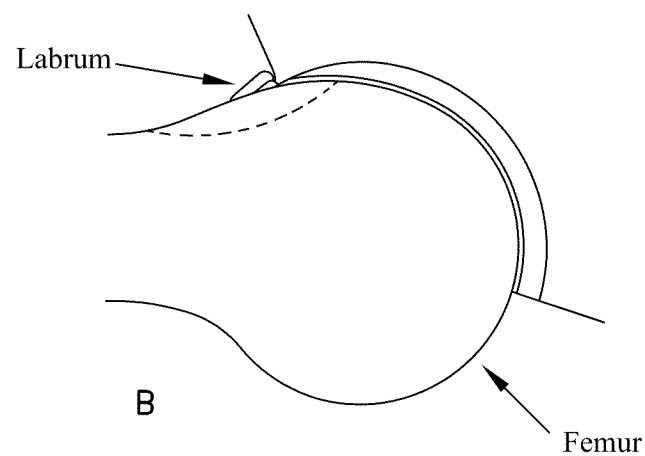
FIG. 13

PINCER-TYPE FEMOROACETABULAR IMPINGEMENT (FAI)
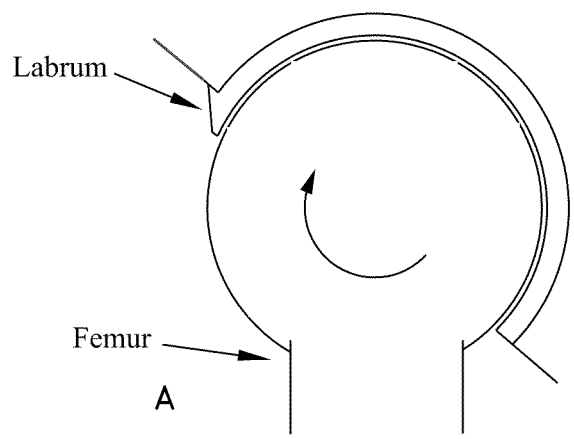
PINCER INJURY TO THE LABRUM
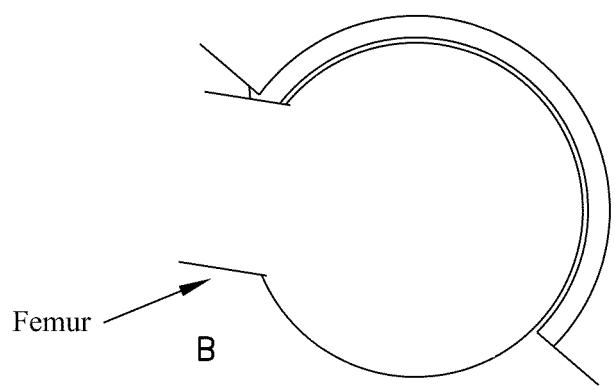
FIG. 14

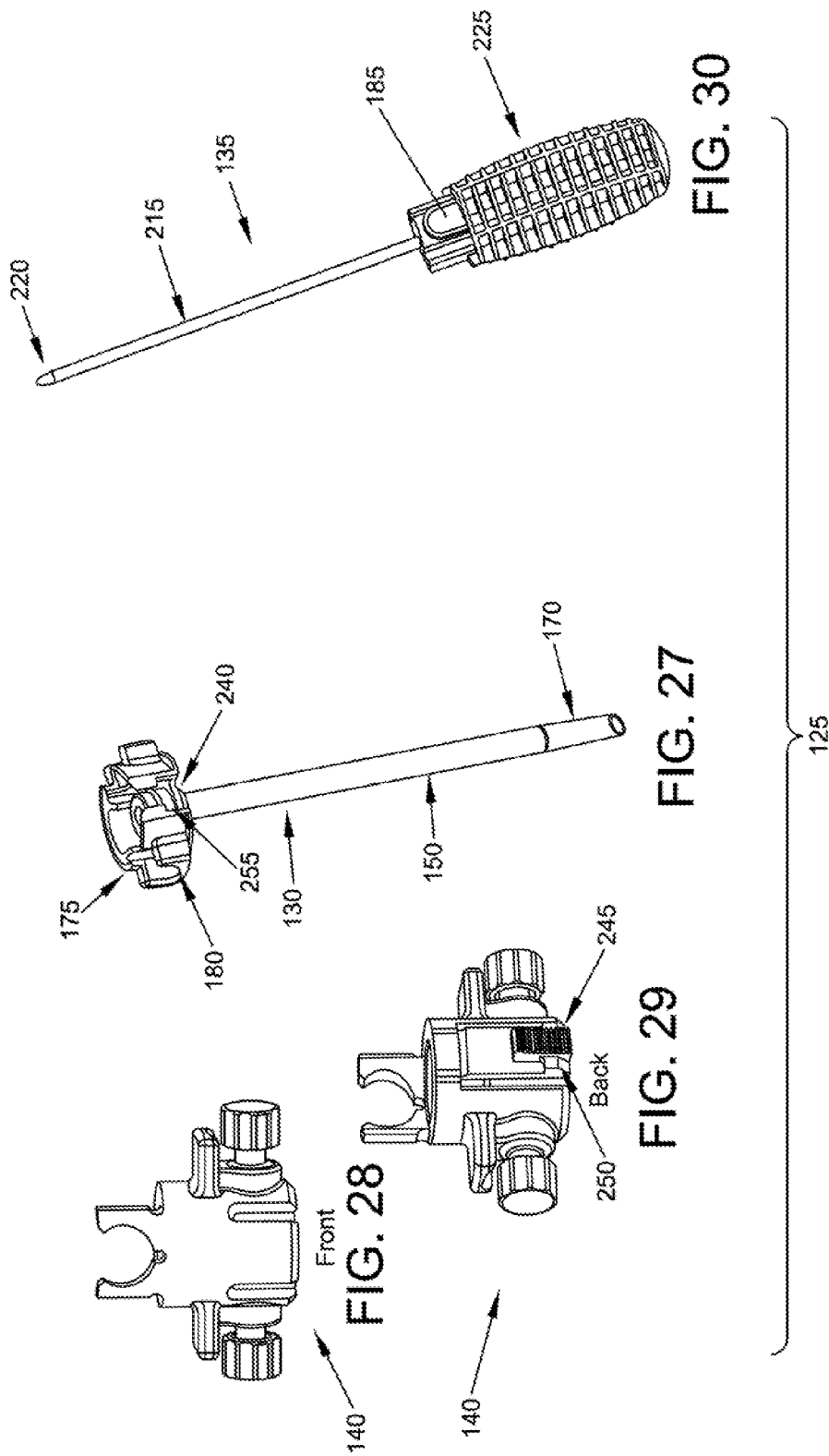

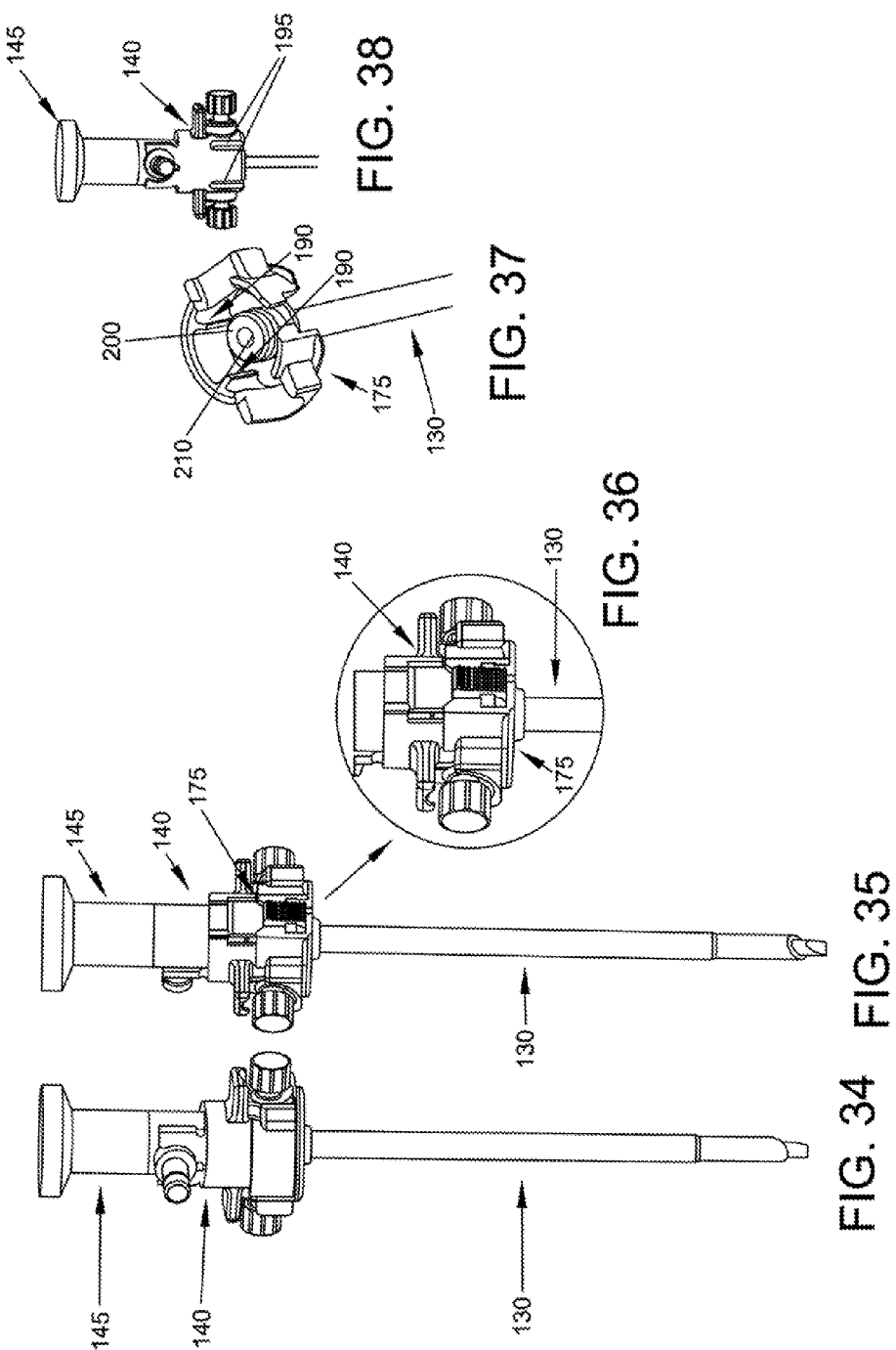

METHOD AND APPARATUS FOR ACCESSING THE INTERIOR OF A HIP JOINT, INCLUDING THE PROVISION AND USE OF A NOVEL INFLOW ACCESS CANNULA

REFERENCE TO PENDING PRIOR PATENT APPLICATION

This patent application claims benefit of prior U.S. Provisional Patent Application Ser. No. 61/361,783, filed Jul. 6, 2010 by Jolene Cutts et al. for METHOD AND APPARATUS FOR ACCESSING THE INTERIOR OF A HIP JOINT, INCLUDING THE PROVISION AND USE OF A NOVEL INFLOW ACCESS CANNULA, which patent application is hereby incorporated herein by reference.

FIELD OF THE INVENTION

This invention relates to surgical methods and apparatus in general, and more particularly to methods and apparatus for treating the hip joint.

BACKGROUND OF THE INVENTION

The Hip Joint in General

The hip joint is a ball-and-socket joint which movably connects the leg to the torso. The hip joint is capable of a wide range of different motions, e.g., flexion and extension, abduction and adduction, medial and lateral rotation, etc. See FIGS. 1A, 1B, 1C and 1D.

With the possible exception of the shoulder joint, the hip joint is perhaps the most mobile joint in the body. Significantly, and unlike the shoulder joint, the hip joint carries substantial weight loads during most of the day, in both static (e.g., standing and sitting) and dynamic (e.g., walking and running) conditions.

The hip joint is susceptible to a number of different pathologies. These pathologies can have both congenital and injury-related origins. In some cases, the pathology can be substantial at the outset. In other cases, the pathology may be minor at the outset but, if left untreated, may worsen over time. More particularly, in many cases, an existing pathology may be exacerbated by the dynamic nature of the hip joint and the substantial weight loads imposed on the hip joint.

The pathology may, either initially or thereafter, significantly interfere with patient comfort and lifestyle. In some cases, the pathology can be so severe as to require partial or total hip replacement. A number of procedures have been developed for treating hip pathologies short of partial or total hip replacement, but these procedures are generally limited in scope due to the significant difficulties associated with treating the hip joint.

A better understanding of various hip joint pathologies, and also the current limitations associated with their treatment, can be gained from a more thorough understanding of the anatomy of the hip joint.

Anatomy of the Hip Joint

The hip joint is formed at the junction of the leg and the hip. More particularly, and looking now at FIG. 2, the head of the femur is received in the acetabular cup of the hip, with a plurality of ligaments and other soft tissue serving to hold the bones in articulating condition.

More particularly, and looking now at FIG. 3, the femur is generally characterized by an elongated body terminating, at its top end, in an angled neck which supports a hemispherical head (also sometimes referred to as "the ball"). As seen in FIGS. 3 and 4, a large projection known as the greater trochanter protrudes laterally and posteriorly from the elongated body adjacent to the neck of the femur. A second, somewhat smaller projection known as the lesser trochanter protrudes medially and posteriorly from the elongated body adjacent to the neck. An intertrochanteric crest (FIGS. 3 and 4) extends along the periphery of the femur, between the greater trochanter and the lesser trochanter.

Looking next at FIG. 5, the hip socket is made up of three constituent bones: the ilium, the ischium and the pubis. These three bones cooperate with one another (they typically ossify into a single "hip bone" structure by the age of 25 or so) in order to collectively form the acetabular cup. The acetabular cup receives the head of the femur.

Both the head of the femur and the acetabular cup are covered with a layer of articular cartilage which protects the underlying bone and facilitates motion. See FIG. 6.

Various ligaments and soft tissue serve to hold the ball of the femur in place within the acetabular cup. More particularly, and looking now at FIGS. 7 and 8, the ligamentum teres extends between the ball of the femur and the base of the acetabular cup. As seen in FIGS. 8 and 9, a labrum is disposed about the perimeter of the acetabular cup. The labrum serves to increase the depth of the acetabular cup and effectively establishes a suction seal between the ball of the femur and the rim of the acetabular cup, thereby helping to hold the head of the femur in the acetabular cup. In addition to the foregoing, and looking now at FIG. 10, a fibrous capsule extends between the neck of the femur and the rim of the acetabular cup, effectively sealing off the ball-and-socket members of the hip joint from the remainder of the body. The foregoing structures (i.e., the ligamentum teres, the labrum and the fibrous capsule) are encompassed and reinforced by a set of three main ligaments (i.e., the iliofemoral ligament, the ischiofemoral ligament and the pubofemoral ligament) which extend between the femur and the perimeter of the hip socket. See, for example, FIGS. 11 and 12, which show the iliofemoral ligament, with FIG. 11 being an anterior view and FIG. 12 being a posterior view.

Pathologies of the Hip Joint

As noted above, the hip joint is susceptible to a number of different pathologies. These pathologies can have both congenital and injury-related origins.

By way of example but not limitation, one important type of congenital pathology of the hip joint involves impingement between the neck of the femur and the rim of the acetabular cup. In some cases, and looking now at FIG. 13, this impingement can occur due to irregularities in the geometry of the femur. This type of impingement is sometimes referred to as cam-type femoroacetabular impingement (i.e., cam-type FAI). In other cases, and looking now at FIG. 14, the impingement can occur due to irregularities in the geometry of the acetabular cup. This latter type of impingement is sometimes referred to as pincer-type femoroacetabular impingement (i.e., pincer-type FAI). Impingement can result in a reduced range of motion, substantial pain and, in some cases, significant deterioration of the hip joint.

By way of further example but not limitation, another important type of congenital pathology of the hip joint involves defects in the articular surface of the ball and/or the articular surface of the acetabular cup. Defects of this type sometimes start out fairly small but often increase in size over time, generally due to the dynamic nature of the hip joint and also due to the weight-bearing nature of the hip joint. Articular defects can result in substantial pain, induce and/or exacerbate arthritic conditions and, in some cases, cause significant deterioration of the hip joint.

By way of further example but not limitation, one important type of injury-related pathology of the hip joint involves trauma to the labrum. More particularly, in many cases, an accident or sports-related injury can result in the labrum being torn away from the rim of the acetabular cup, typically with a tear running through the body of the labrum. See FIG. 15. These types of injuries can be very painful for the patient and, if left untreated, can lead to substantial deterioration of the hip joint.

The General Trend Toward Treating Joint Pathologies Using Minimally-Invasive, and Earlier, Interventions The current trend in orthopedic surgery is to treat joint pathologies using minimally-invasive techniques. Such minimally-invasive, "keyhole" surgeries generally offer numerous advantages over traditional, "open" surgeries, including reduced trauma to tissue, less pain for the patient, faster recuperation times, etc.

By way of example but not limitation, it is common to re-attach ligaments in the shoulder joint using minimally-invasive, "keyhole" techniques which do not require laying open the capsule of the shoulder joint. By way of further example but not limitation, it is common to repair torn meniscal cartilage in the knee joint, and/or to replace ruptured ACL ligaments in the knee joint, using minimally-invasive techniques.

While such minimally-invasive approaches can require additional training on the part of the surgeon, such procedures generally offer substantial advantages for the patient and have now become the standard of care for many shoulder joint and knee joint pathologies.

In addition to the foregoing, in view of the inherent advantages and widespread availability of minimally-invasive approaches for treating pathologies of the shoulder joint and knee joint, the current trend is to provide such treatment much earlier in the lifecycle of the pathology, so as to address patient pain as soon as possible and so as to minimize any exacerbation of the pathology itself. This is in marked contrast to traditional surgical practices, which have generally dictated postponing surgical procedures as long as possible so as to spare the patient from the substantial trauma generally associated with invasive surgery.

Treatment for Pathologies of the Hip Joint

Unfortunately, minimally-invasive treatments for pathologies of the hip joint have lagged far behind minimally-invasive treatments for pathologies of the shoulder joint and the knee joint. This is generally due to (i) the constrained geometry of the hip joint itself, and (ii) the nature and location of the pathologies which must typically be addressed in the hip joint.

More particularly, the hip joint is generally considered to be a "tight" joint, in the sense that there is relatively little room to maneuver within the confines of the joint itself. This is in marked contrast to the shoulder joint and the knee joint, which are generally considered to be relatively "spacious" joints (at least when compared to the hip joint). As a result, it is relatively difficult for surgeons to perform minimally-invasive procedures on the hip joint.

Furthermore, the pathways for entering the interior of the hip joint (i.e., the natural pathways which exist between adjacent bones and/or delicate neurovascular structures) are generally much more constraining for the hip joint than for the shoulder joint or the knee joint. This limited access further complicates effectively performing minimally-invasive procedures on the hip joint.

In addition to the foregoing, the nature and location of the pathologies of the hip joint also complicate performing minimally-invasive procedures on the hip joint. By way of example but not limitation, consider a typical detachment of the labrum in the hip joint. In this situation, instruments must generally be introduced into the joint space using an angle of approach which is offset from the angle at which the instrument addresses the tissue. This makes drilling into bone, for example, significantly more complicated than where the angle of approach is effectively aligned with the angle at which the instrument addresses the tissue, such as is frequently the case in the shoulder joint. Furthermore, the working space within the hip joint is typically extremely limited, further complicating repairs where the angle of approach is not aligned with the angle at which the instrument addresses the tissue.

As a result of the foregoing, minimally-invasive hip joint procedures are still relatively difficult to perform and relatively uncommon in practice. Consequently, patients are typically forced to manage their hip pain for as long as possible, until a resurfacing procedure or a partial or total hip replacement procedure can no longer be avoided. These procedures are generally then performed as a highly-invasive, open procedure, with all of the disadvantages associated with highly-invasive, open procedures.

As a result, there is, in general, a pressing need for improved methods and apparatus for treating pathologies of the hip joint.

Arthroscopic Access to the Interior of the Hip Joint

Successful hip arthroscopy generally requires safe and effective access to the interior of the hip joint. More particularly, successful hip arthroscopy generally requires the creation of a plurality of access portals which extend from the surface of the skin, down through the intervening tissue, and then into the interior of the hip joint. Depending on the specific surgical site which is to be accessed within the interior of the hip joint, different anatomical pathways may be utilized for the access portals. By way of example but not limitation, one anatomical pathway may be used where a torn labrum is to be repaired, and another anatomical pathway may be used where the lesser trochanter must be addressed. And, in most cases, multiple access portals are generally required, with one access portal being used for visualization (i.e., to introduce an arthroscope into the interior of the hip joint), while other access portals are used to pass surgical instruments to and from the surgical site, etc.

Establishing these access portals typically involves forming an opening from the top surface of the skin down to the interior of the joint, and lining that opening with a tubular liner (sometimes referred to as an "access cannula"). This access cannula holds the incision open and provides a surgical pathway (or "corridor") from the top surface of the skin down to the interior of the hip joint, thereby enabling keyhole surgery to be performed on the hip joint.

Prior Art Access Cannulas

Access cannulas of the sort discussed above are well known in the art. However, such prior art access cannulas are typically designed to serve a wide range of different purposes and, as a result, often perform certain specific tasks in a fairly mediocre manner, e.g., initial access creation and endoscope support. Furthermore, such prior art access cannulas typically have distal ends which can cause substantial trauma to tissue when they come into contact with tissue, e.g., during cannula insertion. In addition, such prior art access cannulas are typically relatively inefficient in their use of space, and hence cover a substantial portion of an instrument's length, thereby reducing access of the instrument to deep surgical sites within the joint space.

The Need for a New and Improved Access Cannula

On account of the foregoing, it will be appreciated that there is a need for a new and improved access cannula which can overcome the deficiencies of prior art access cannulas.

Among other things, there is a need for a new and improved access cannula which can perform certain specific tasks unusually well (e.g., initial access creation and endoscope support), has a distal end which is relatively atraumatic when it comes into contact with tissue, and which is highly efficient in its use of space so as to cover a reduced portion of an instrument's length, thereby increasing access of the instrument to deep surgical sites within the joint space.

SUMMARY OF THE INVENTION

These and other objects of the present invention are addressed by the provision and use of a new and improved inflow access cannula for accessing the interior of a hip joint or other interior body space.

Among other things, this new and improved inflow access cannula can perform certain specific tasks unusually well (e.g., initial access creation and endoscope support), has a distal end which is relatively atraumatic when it comes into contact with tissue, and which is highly efficient in its use of space so as to cover a reduced portion of an instrument's length, thereby increasing access of the instrument to deep surgical sites within the joint space.

In one form of the present invention, there is provided an inflow access cannula system for allowing an instrument to access a remote surgical site, wherein the instrument comprises a distal portion having a smaller diameter and a proximal portion having a larger diameter, the system comprising:

an inflow access cannula comprising a distal end, a proximal end and a central lumen extending therebetween, wherein the central lumen has a diameter larger than the distal portion of the instrument and smaller than the proximal portion of the instrument; and an instrument adapter for releasable connection to the inflow access cannula, the instrument adapter comprising a lumen communicating with the central lumen of the inflow access cannula, the lumen having a diameter larger than the proximal portion of the instrument, the instrument adapter further comprising a port and a fluid passageway connecting the port with the lumen of the instrument adapter, and a spacer for spacing the proximal portion of the instrument from the distal end of the inflow access cannula, such that when an instrument is disposed in the inflow access cannula system so that the distal portion of the instrument extends within the central lumen of the inflow access cannula and the proximal portion of the instrument is disposed in the central lumen of the instrument adapter and is in engagement with the spacer, fluid can flow into the port of the instrument adapter, along the fluid passageway of the instrument adapter, into the lumen of the instrument adapter and through the lumen of the inflow access cannula.

In another form of the present invention, there is provided an inflow access cannula comprising:

an elongated body comprising a distal end, a proximal end and a lumen extending therebetween, the distal end of the elongated body comprising an atraumatic tip.

In another form of the present invention, there is provided a method for accessing a remote surgical site with an instrument, wherein the instrument comprises a distal portion having a smaller diameter and a proximal portion having a larger diameter, the method comprising:

providing an inflow access cannula system comprising:
an inflow access cannula comprising a distal end, a proximal end and a central lumen extending therebetween, wherein the central lumen has a diameter larger than the distal portion of the instrument and smaller than the proximal portion of the instrument; and
an instrument adapter for releasable connection to the inflow access cannula, the instrument adapter comprising a lumen communicating with the central lumen of the inflow access cannula, the lumen having a diameter larger than the proximal portion of the instrument, the instrument adapter further comprising a port and a fluid passageway connecting the port with the lumen of the instrument adapter, and a spacer for spacing the proximal portion of the instrument from the distal end of the inflow access cannula, such that when an instrument is disposed in the inflow access cannula system so that the distal portion of the instrument extends within the central lumen of the inflow access cannula and the proximal portion of the instrument is disposed in the central lumen of the instrument adapter and is in engagement with the spacer, fluid can flow into the port of the instrument adapter, along the fluid passageway of the instrument adapter, into the lumen of the instrument adapter and through the lumen of the inflow access cannula;

advancing the inflow access cannula system through tissue to the surgical site; and advancing the instrument into the inflow access cannula system.

In another form of the present invention, there is provided a method for accessing a remote surgical site with an instrument, wherein the instrument comprises a distal portion having a smaller diameter and a proximal portion having a larger diameter, the method comprising:

providing an inflow access cannula system comprising:
an inflow access cannula comprising a distal end, a proximal end and a central lumen extending therebetween, wherein the central lumen has a diameter larger than the distal portion of the instrument and smaller than the proximal portion of the instrument; and
an instrument adapter for releasable connection to the inflow access cannula, the instrument adapter comprising a lumen communicating with the central lumen of the inflow access cannula, the lumen having a diameter larger than the proximal portion of the instrument, the instrument adapter further comprising a port and a fluid passageway connecting the port with the lumen of the instrument adapter, and a spacer for spacing the proximal portion of the instrument from the distal end of the inflow access cannula, such that when an instrument is disposed in the inflow access cannula system so that the distal portion of the instrument extends within the central lumen of the inflow access cannula and the proximal portion of the instrument is disposed in the central lumen of the instrument adapter and is in engagement with the spacer, fluid can flow into the port of the instrument adapter, along the fluid passageway of the instrument adapter, into the lumen of the instrument adapter and through the lumen of the inflow access cannula;

advancing the inflow access cannula through tissue to the surgical site;

mounting the instrument adapter to the instrument; and advancing the instrument into the inflow access cannula so that the instrument adapter mounts to the inflow access cannula.

In another form of the present invention, there is provided an access cannula system for allowing an instrument to access a remote surgical site, the system comprising:

an access cannula;

an instrument adapter for releasable connection to the access cannula, the instrument adapter being adapted to mate with an instrument to be extended through the lumen of the access cannula; and wherein the instrument adapter is releasably mounted to the access cannula by a bayonet mount.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts, and further wherein:

FIG. 13 is a schematic view showing cam-type femoroacetabular impingement (FAI);

FIG. 14 is a schematic view showing pincer-type femoroacetabular impingement (FAI);

FIGS. 27-42 are schematic views showing another preferred form of inflow access cannula system formed in accordance with the present invention.

DETAILED DESCRIPTION OF THE PREFERRED EMBODIMENTS

Figure 1A:
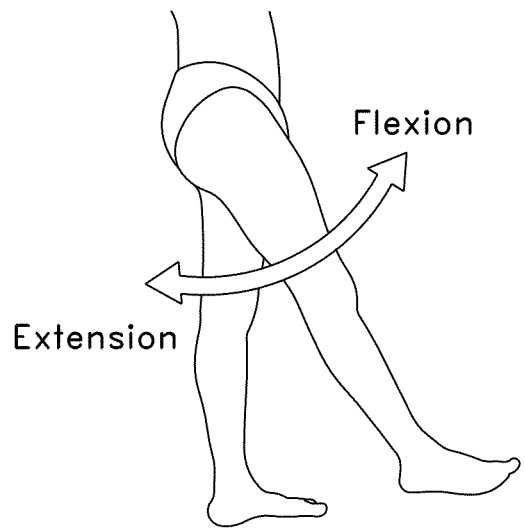
FIGS. 1A-1D are schematic views showing various aspects of hip motion.
Figure 1B:
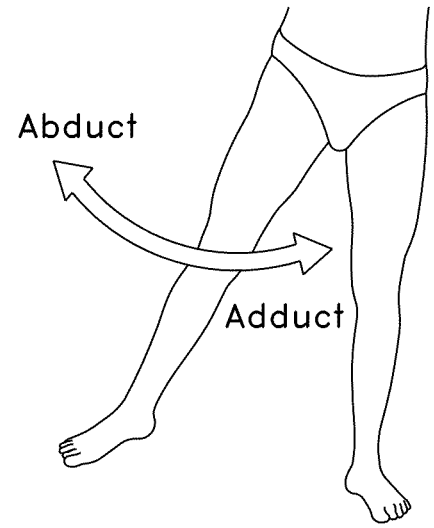
Figure 1C:
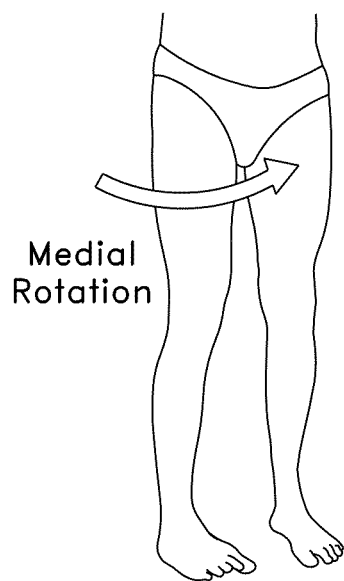
Figure 1D:
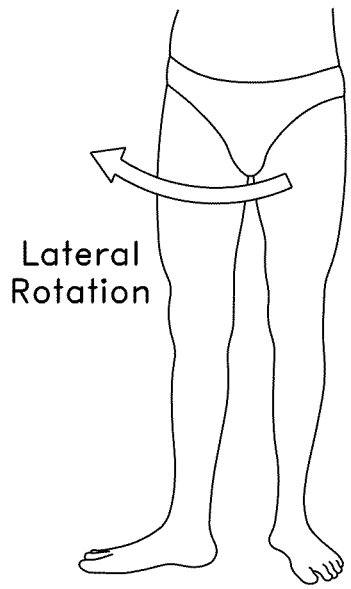
Figure 2:
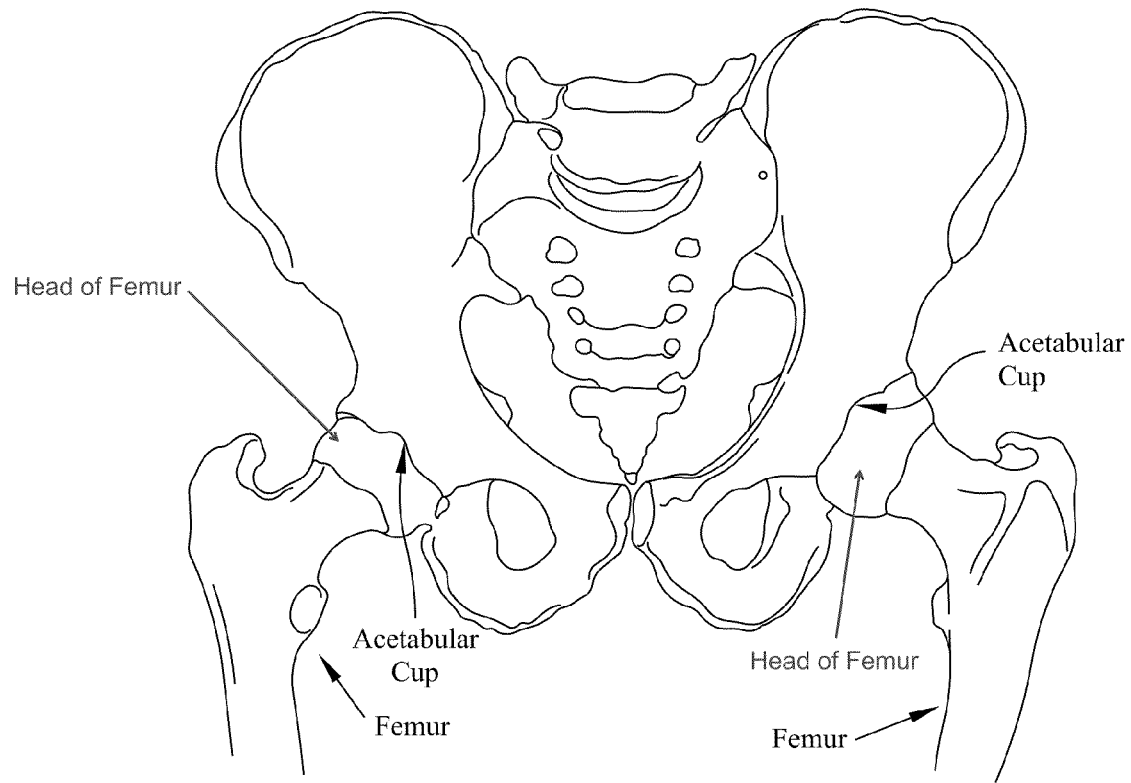
FIG. 2 is a schematic view showing the bone structure in the region of the hip joints.
Figure 3:
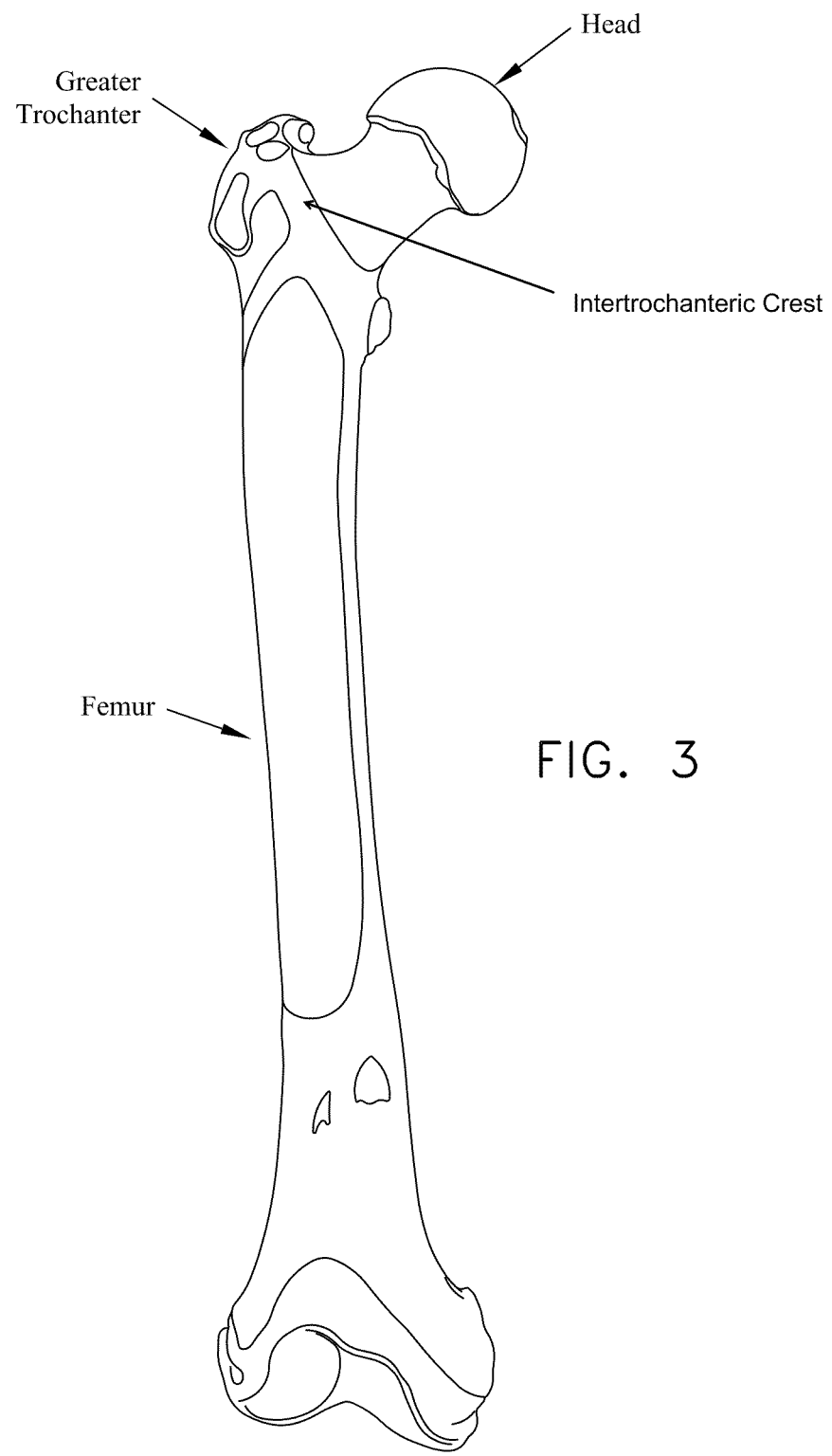
FIG. 3 is a schematic view of the femur.
Figure 4:
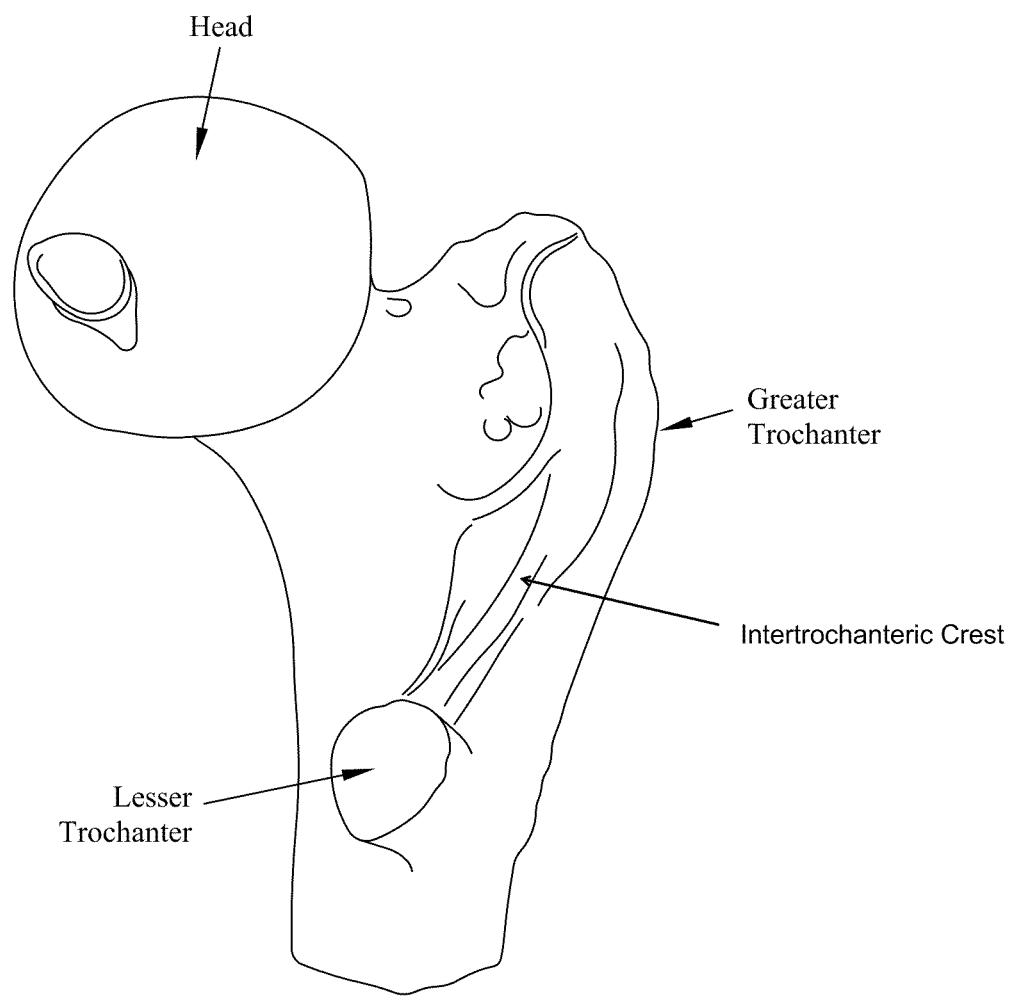
FIG. 4 is a schematic view of the top end of the femur.
Figure 5:
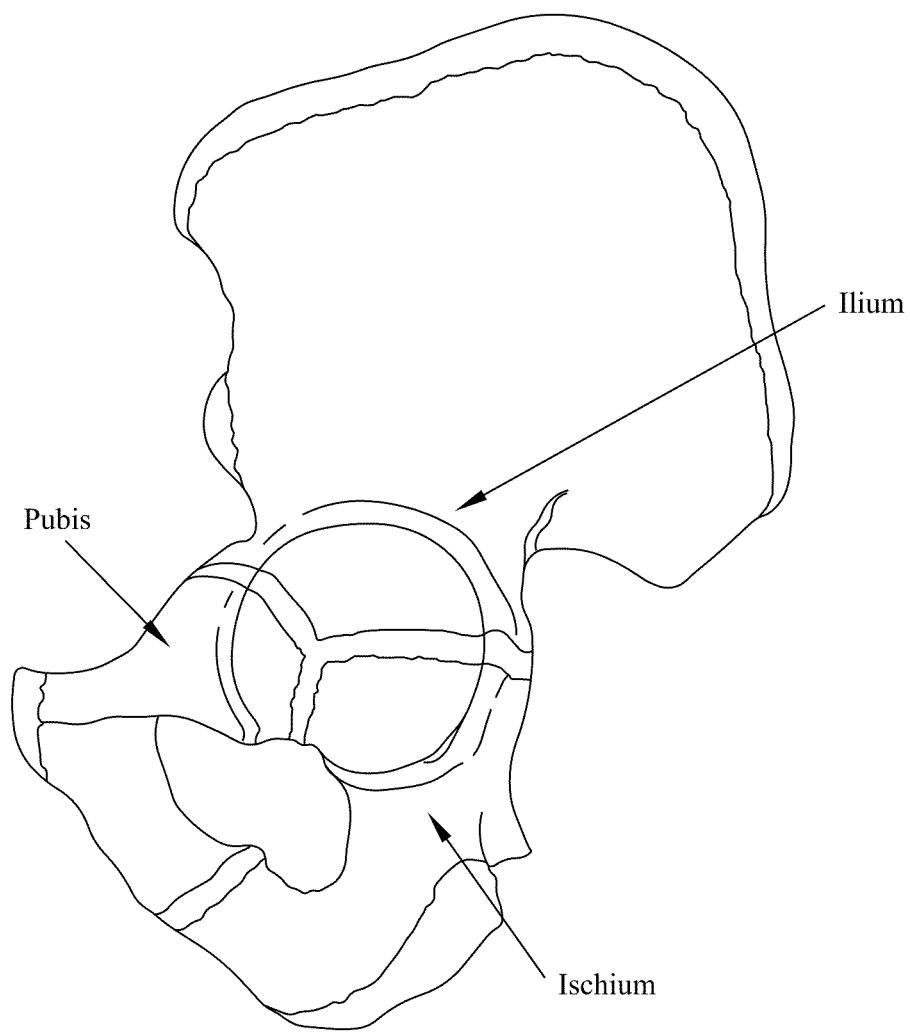
FIG. 5 is a schematic view of the pelvis.
Figure 6:
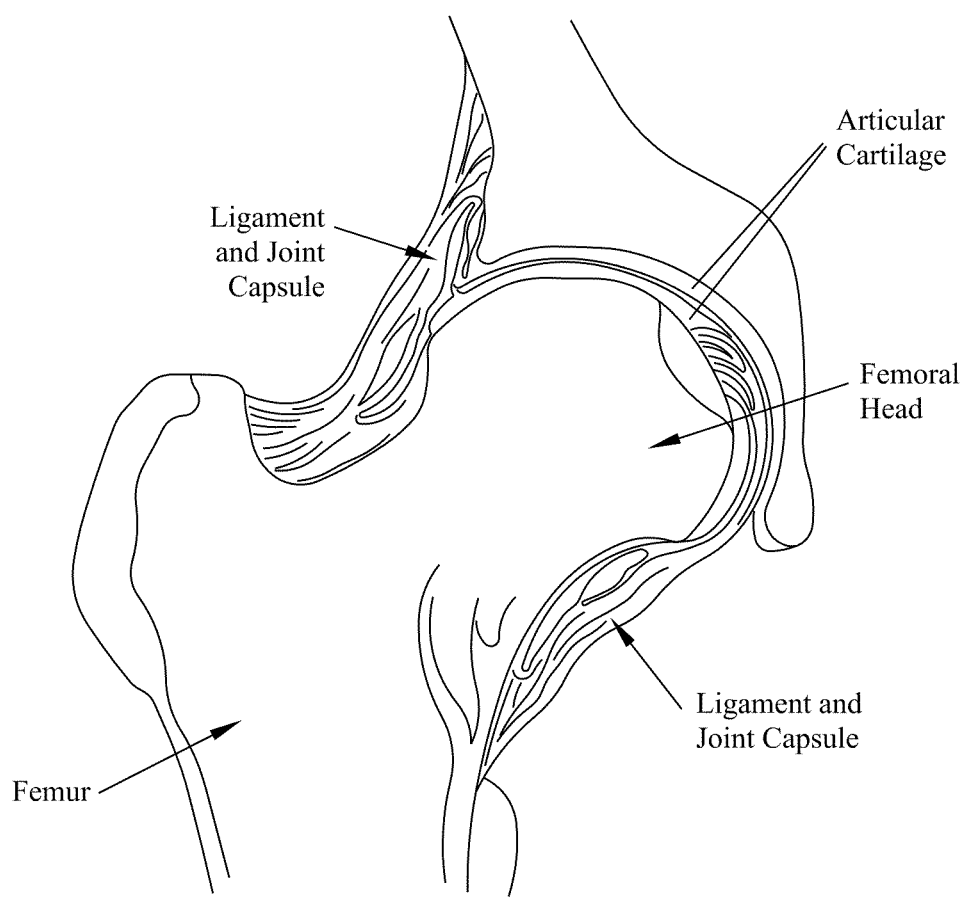
FIGS. 6-12 are schematic views showing the bone and soft tissue structure of the hip joint.
Figure 7:
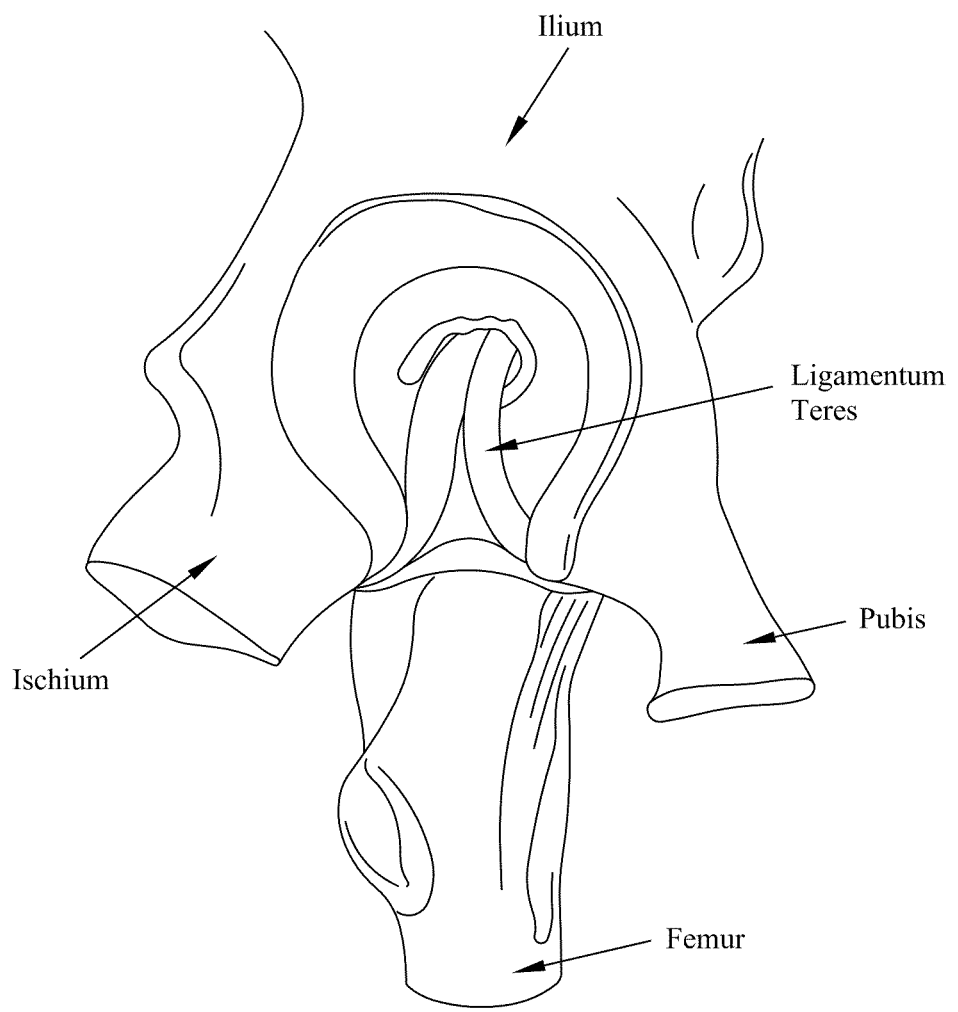
Figure 8:
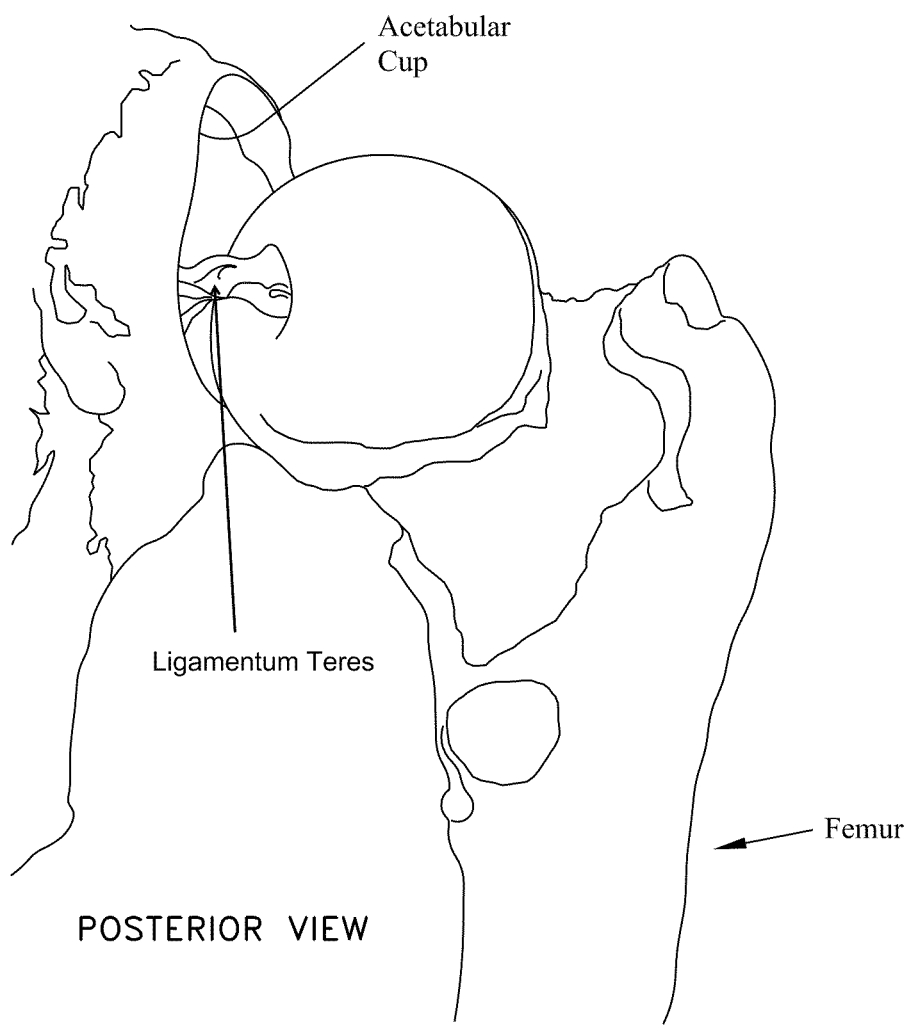
Figure 9:
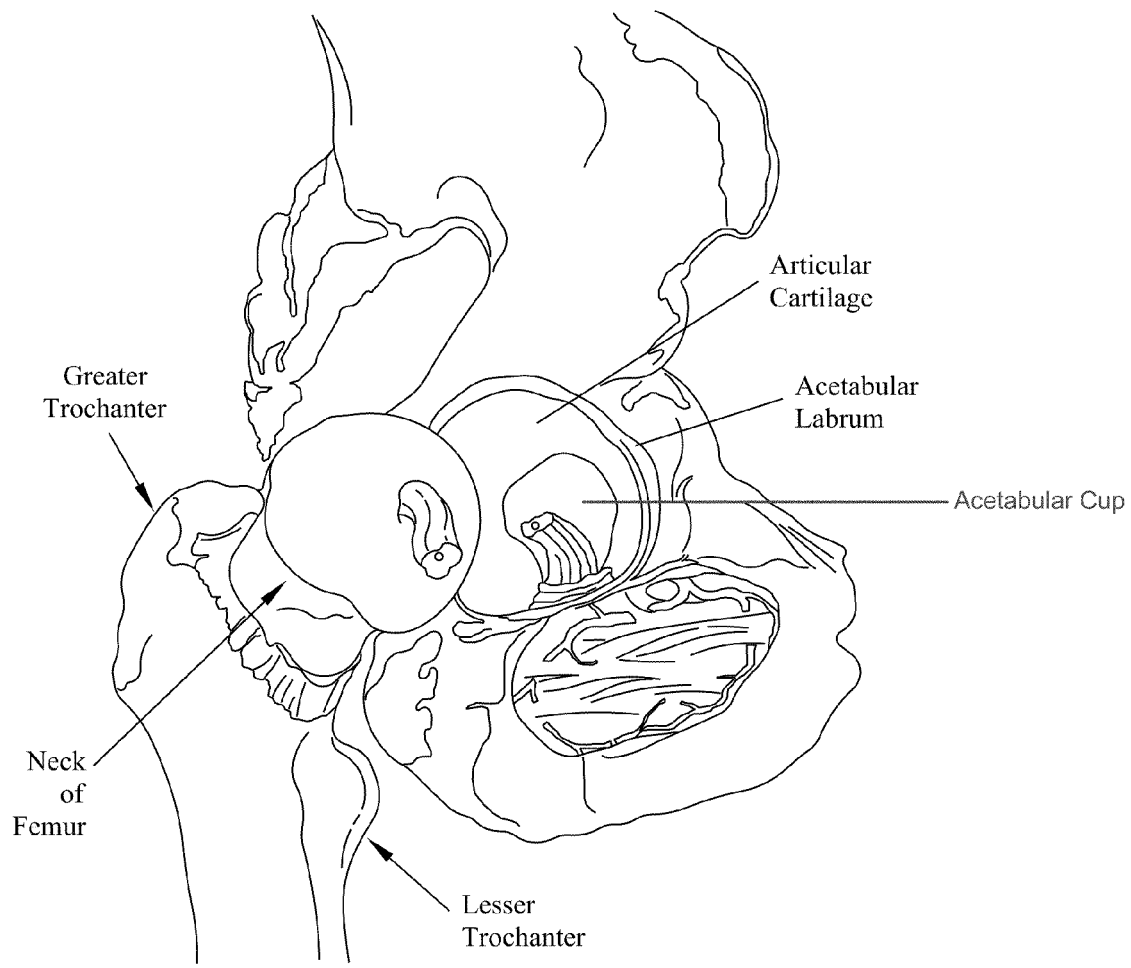
Figure 10:
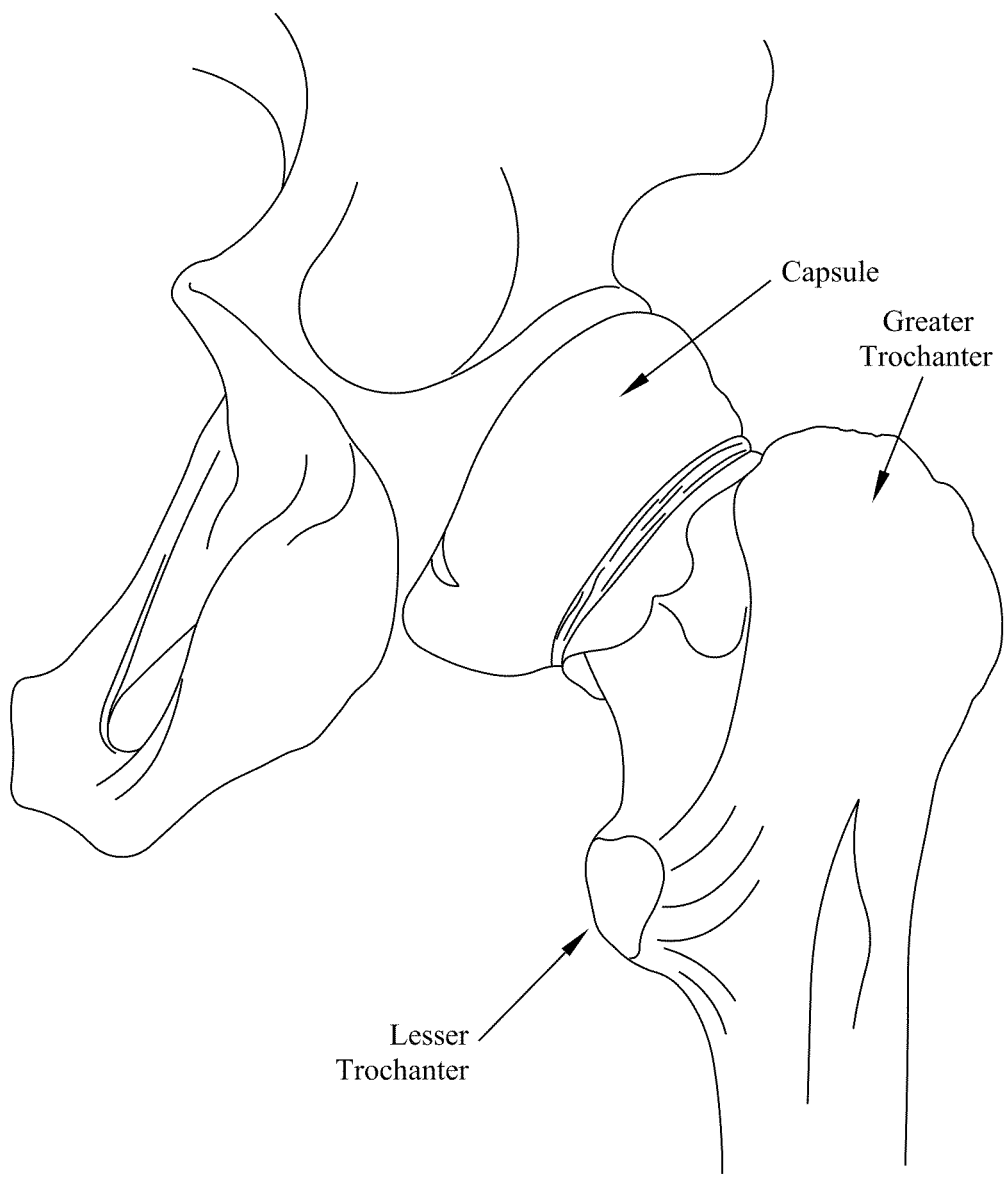
Figure 11:
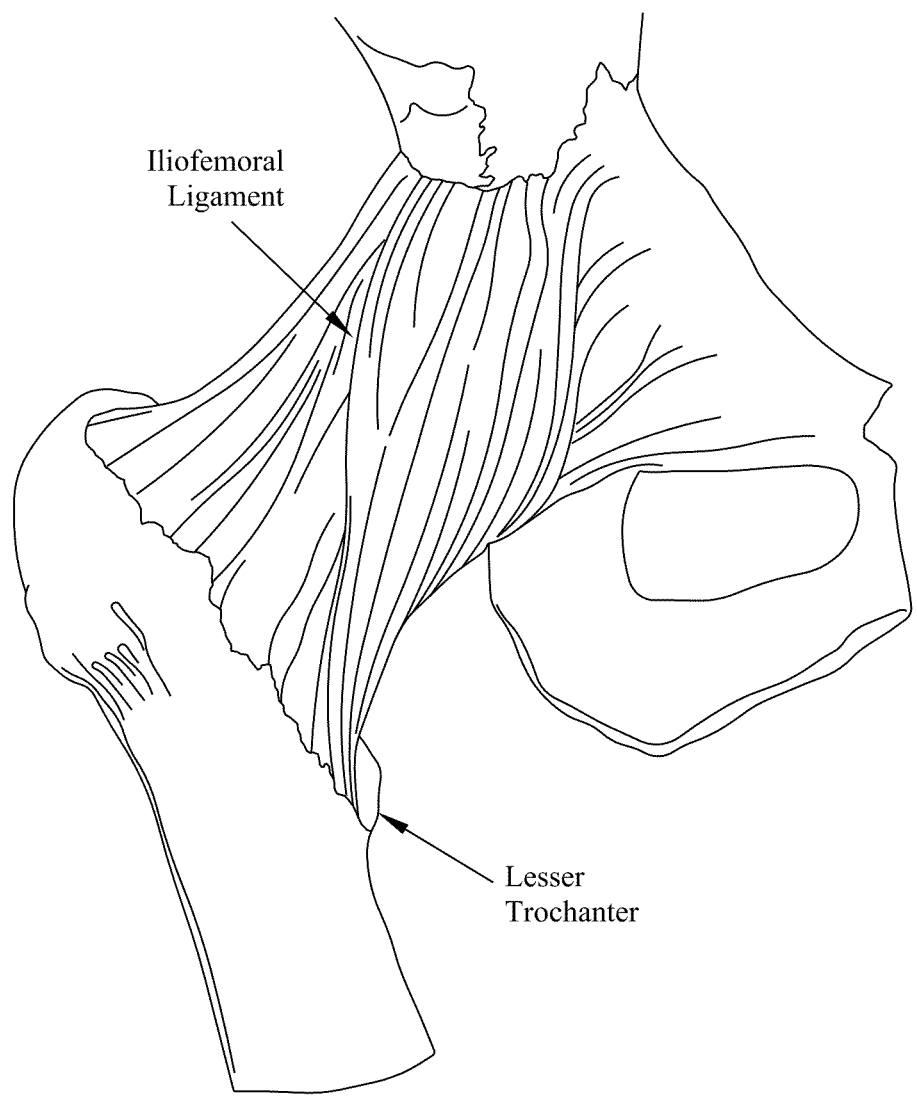
Figure 12:
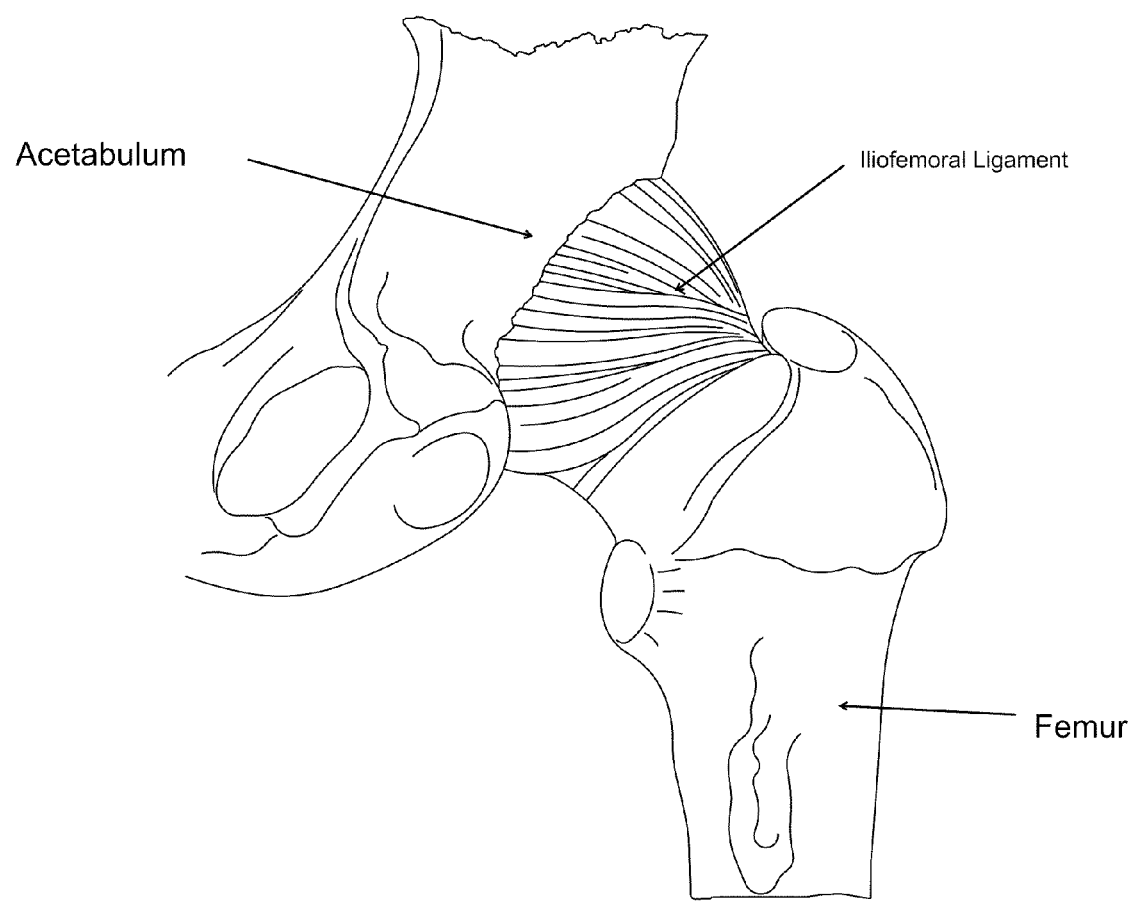
Figure 15:
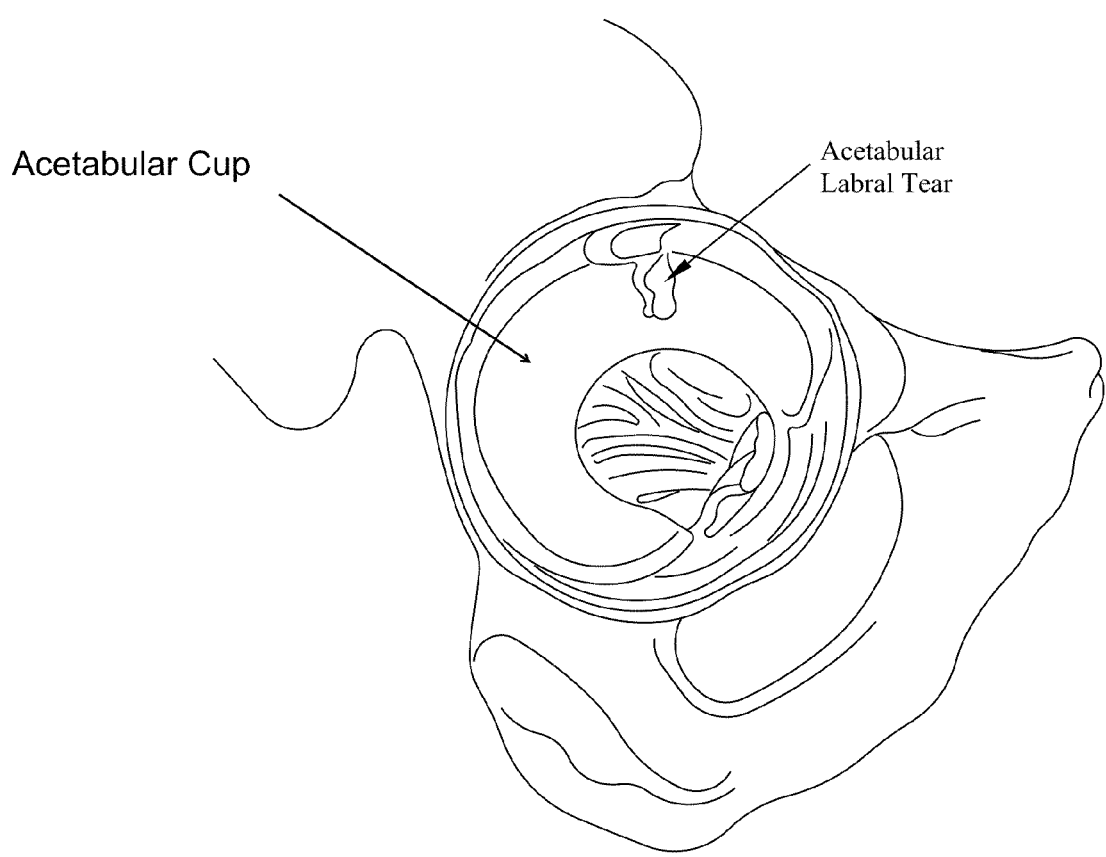
FIG. 15 is a schematic view showing a labral tear.
Figure 16:
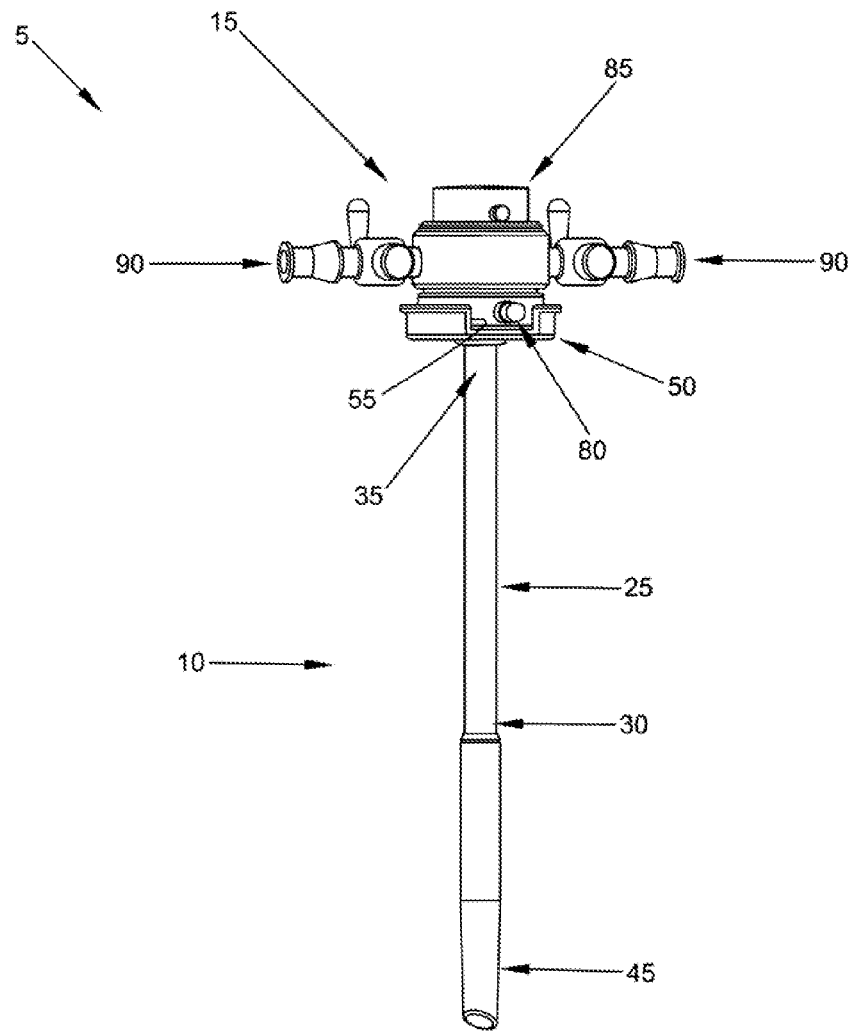
FIGS. 16-26 are schematic views showing one preferred form of inflow access cannula system formed in accordance with the present invention.
Figure 17:
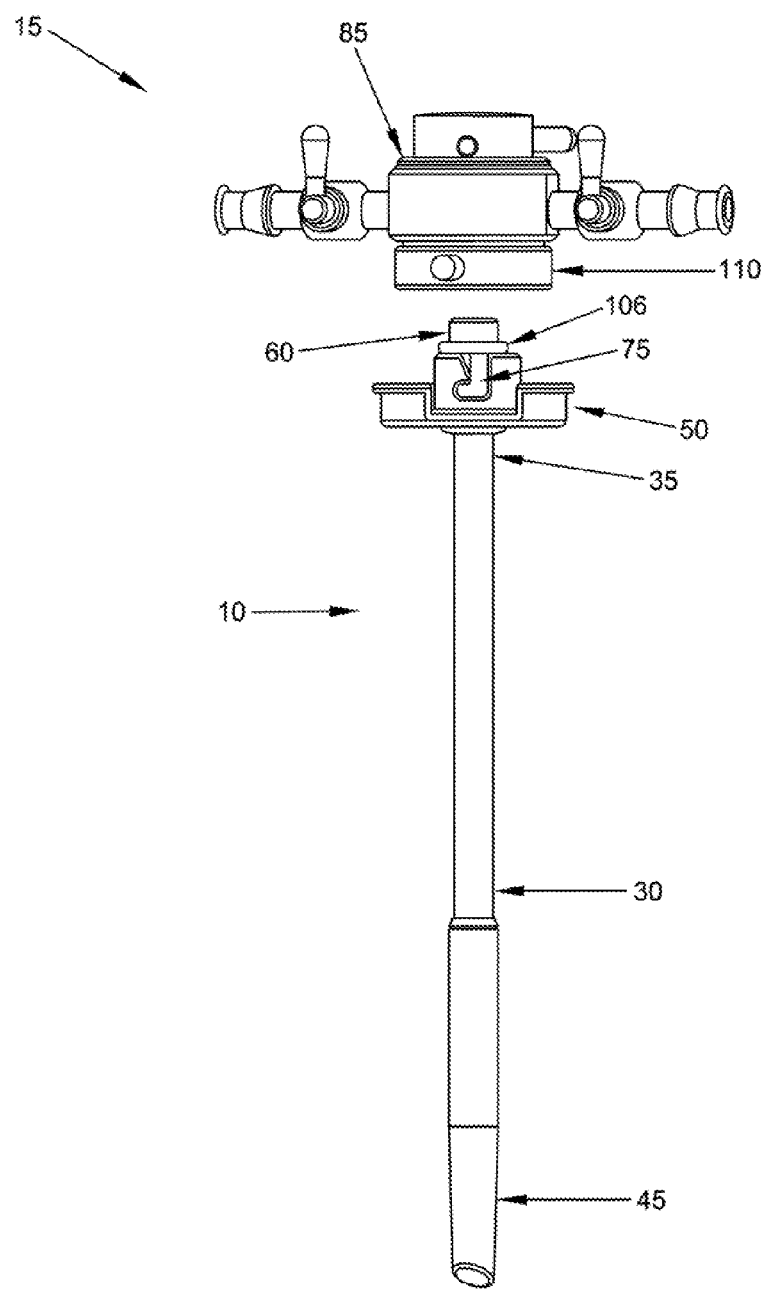
Figure 18:
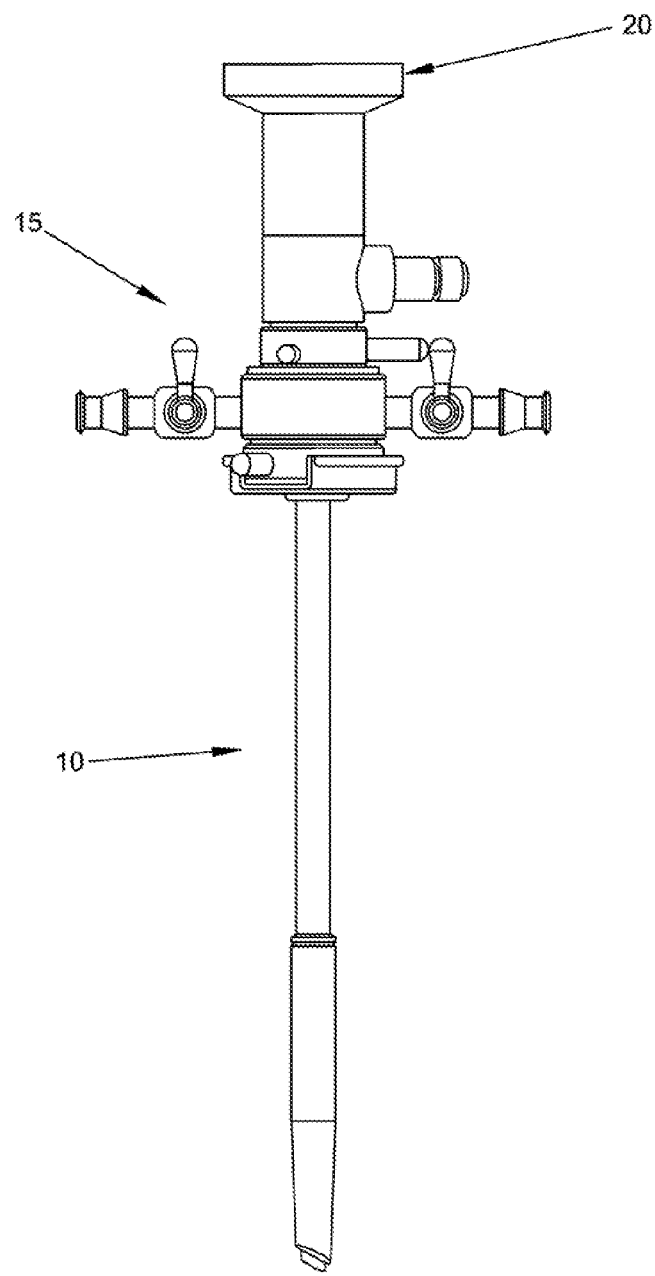
Figure 19:
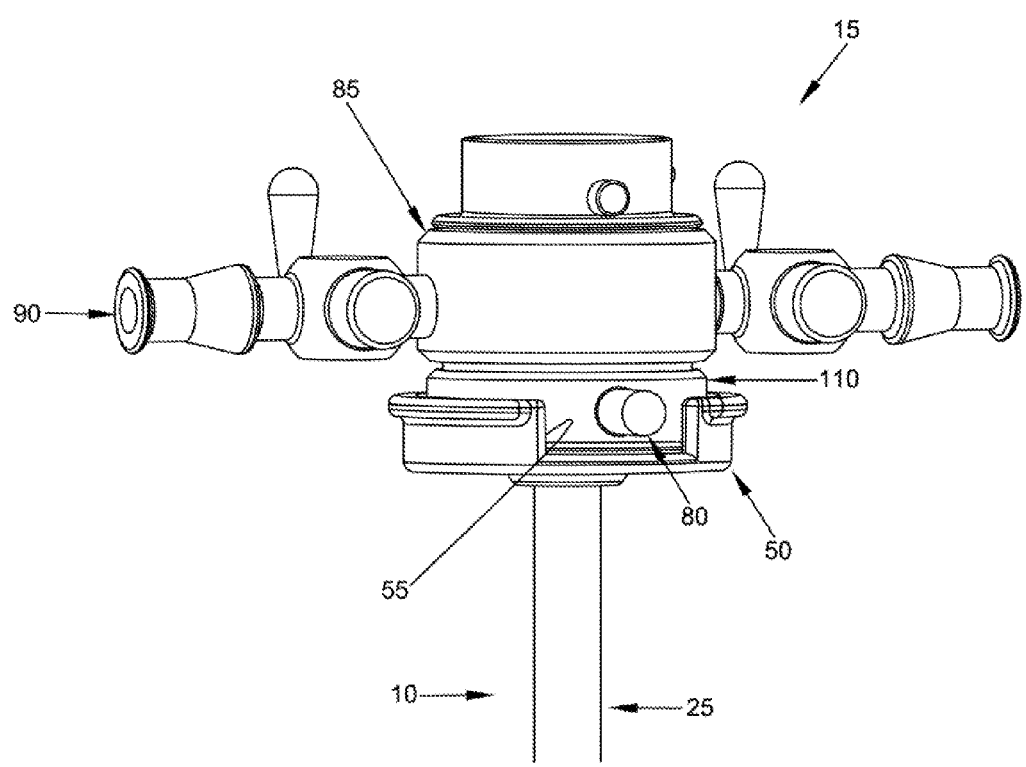
Figure 20:
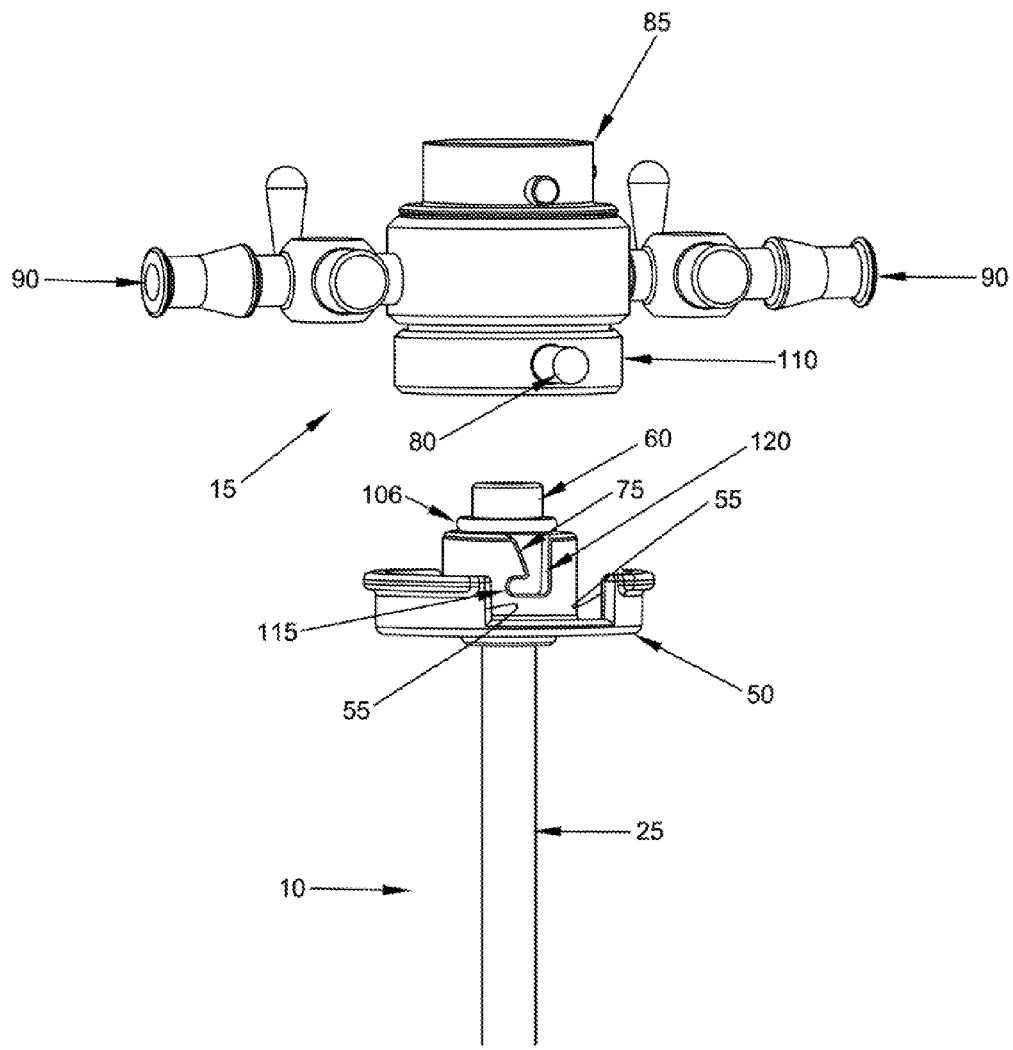
Figure 21:
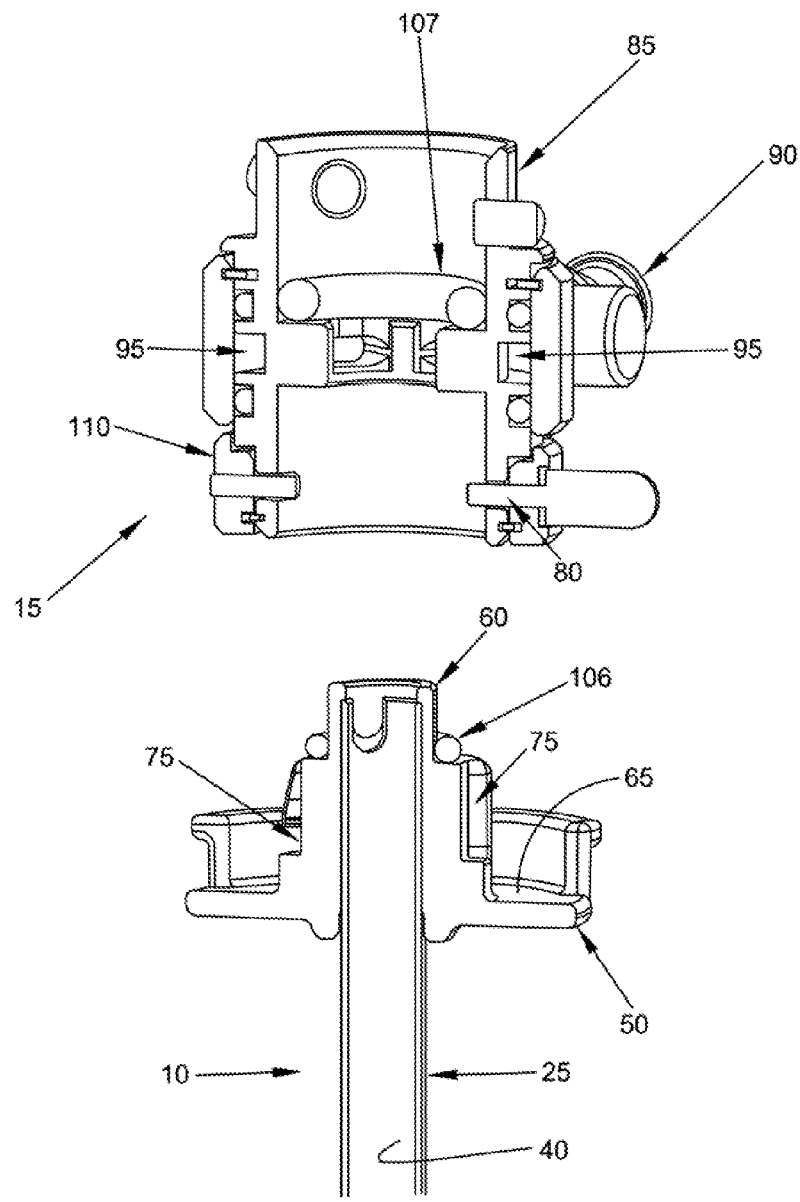
Figure 22:
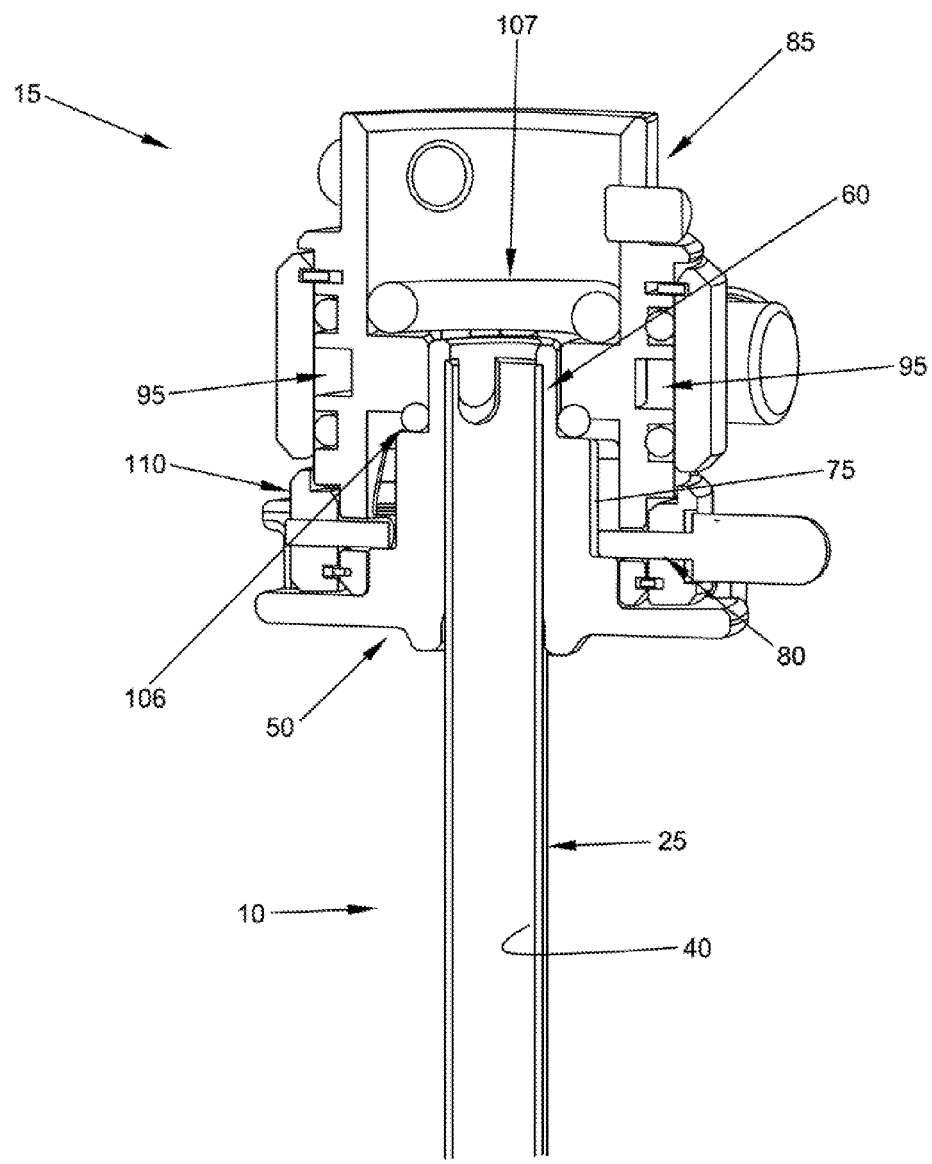
Figure 23:
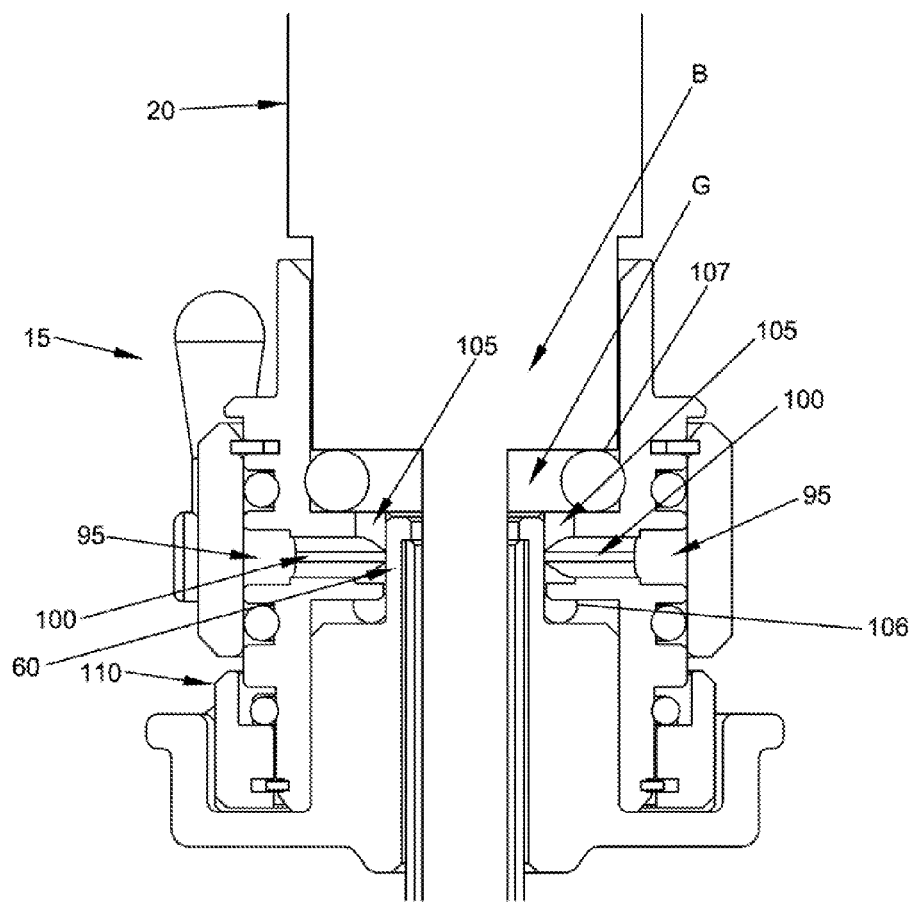
Figure 24:
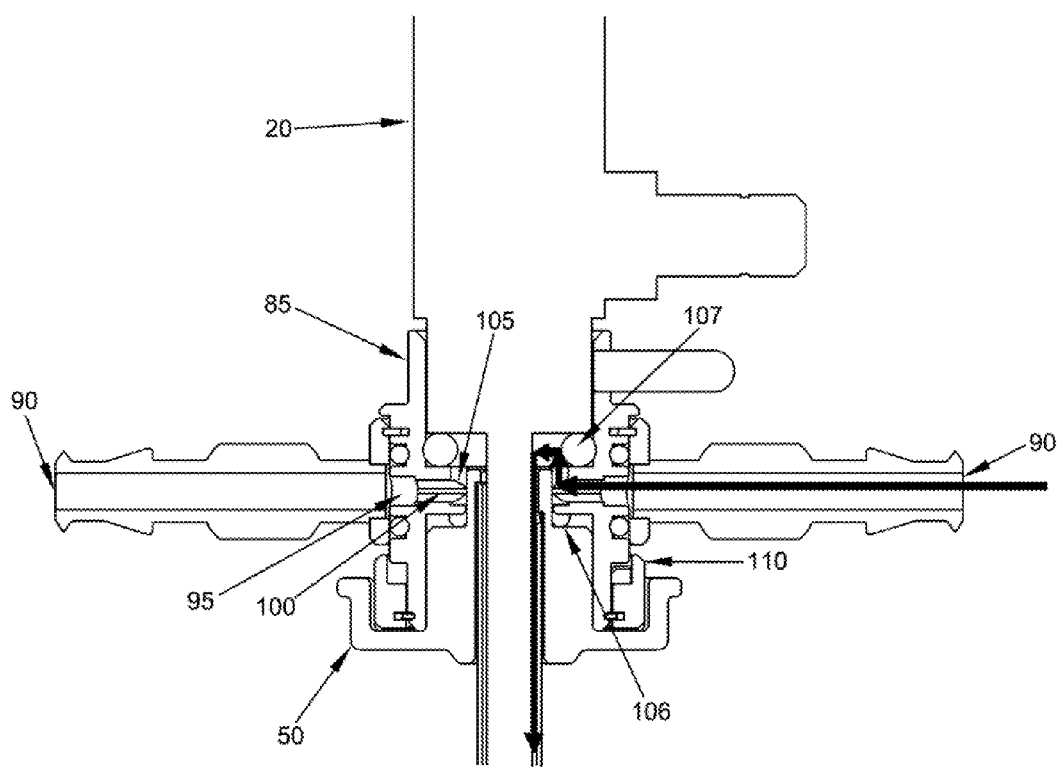
Figure 25:
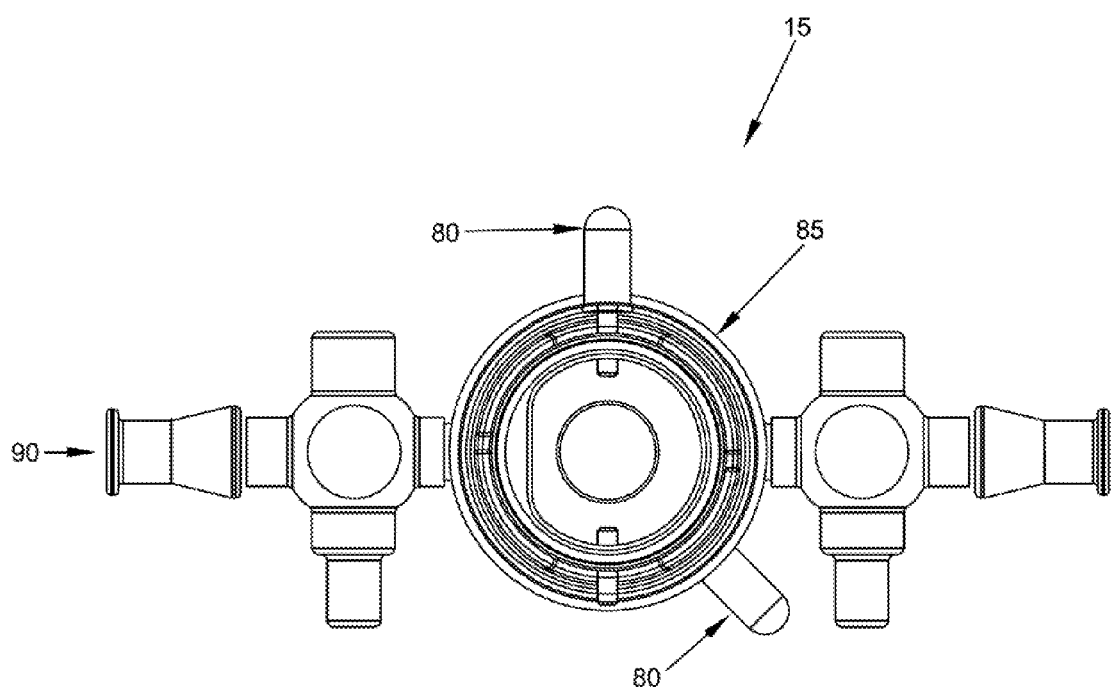

The present invention provides a new and improved inflow access cannula system for accessing the interior of a hip joint or other interior body space.

Among other things, this new and improved inflow access cannula can perform certain specific tasks unusually well (e.g., initial access creation and endoscope support), has a distal end which is relatively atraumatic when it comes into contact with tissue, and which is highly efficient in its use of space so as to cover a reduced portion of an instrument's length, thereby increasing access of the instrument to deep surgical sites within the joint space.

Looking now at FIGS. 16-26, there is shown an inflow access cannula system 5 which generally comprises an inflow access cannula 10 and an endoscope adapter 15.

In accordance with the present invention, an obturator (not shown) is intended to be positioned within inflow access cannula 10, and the inflow access cannula is intended to be inserted into the tissue of a patient so that the distal end of the inflow access cannula is disposed within the hip joint and the proximal end of the inflow access cannula is disposed at the surface of the skin. When inflow access cannula 10 has been properly positioned in the tissue of the patient, the obturator is removed, endoscope adapter 15 is positioned on the proximal end of inflow access cannula 10, and an endoscope 20 is advanced through the central lumen of the endoscope adapter and the central lumen of the inflow access cannula, whereby to provide visualization of, and fluid flow to and/or from, a remote surgical site. Alternatively, endoscope adapter 15 may be mounted on endoscope 20 remote from inflow access cannula 10 and then the two elements (i.e., the endoscope and the endoscope adapter) advanced together as a unit so as to seat on inflow access cannula 10.

More particularly, inflow access cannula 10 generally comprises an elongated tube 25 having a distal end 30, a proximal end 35 and a central lumen 40 (FIG. 21) extending therebetween. The shaft of elongated tube 25 is long enough so that it can extend between the outer surface of the patient's skin and the interior of the joint. Furthermore, the shaft of elongated tube 25 is preferably formed out of metal (e.g., stainless steel) so as to provide strength and rigidity during insertion of the inflow access cannula into the tissue of the patient and its subsequent use as a liner for the access corridor extending down to the remote surgical site. Alternatively, the shaft of elongated tube 25 may be a metal tube coaxial with a plastic tube, the metal tube being disposed either inside of, or outside of, the plastic tube. The outer surface of elongated tube 25 is preferably smooth so as to minimize trauma to tissue as inflow access cannula 10 is inserted in the tissue.

Distal end 30 of inflow access cannula 10 preferably comprises a soft, atraumatic distal tip 45 so as to also minimize tissue trauma during cannula insertion and use.

In one preferred form of the invention, at least the atraumatic distal tip 45 of inflow access cannula 10 comprises a polymer or other material which contains barium sulfate, preferably in the range of 5-30% (and preferably about 15%) by weight, so as to render the inflow access cannula visible under X-ray or fluoroscopy. This range (by weight) of barium sulfate is generally preferred since concentrations below 5% tend to be too low for good visualization in hip applications, whereas concentrations above 30% can lead to degradation of material properties. Alternatively, other opacifiers, at appropriate weight concentrations, may also be used to render the inflow access cannula visible under X-ray or fluoroscopy. Atraumatic distal tip 45 can be a thermoplastic which is over-molded onto the distal end of elongated tube 25 (see FIGS. 16 and 17).

A mount 50 is secured to proximal end 35 of elongated tube 25. Mount 50 includes a keyway 55 for receiving a corresponding key (not shown) of an obturator (also not shown), whereby to releasably rotatably lock the obturator to inflow access cannula 10, e.g., so as to permit rotational driving deployment of the inflow access cannula into the tissue via the obturator. Mount 50 also includes a stem 60 (FIG. 21) which protrudes upward from the floor 65 of mount 50. Stem 60 includes a lumen 70 (FIG. 26) which communicates with central lumen 40 (FIG. 21) of elongated tube 25. Stem 60 also includes an L-shaped keyway 75 (FIG. 17) which receives corresponding keys 80 provided on endoscope adapter 15, whereby to releasably axially lock endoscope adapter 15 to inflow access cannula 10, as will hereinafter be discussed in further detail.

Endoscope adapter 15 comprises a body 85 which is adapted to mate with mount 50 of inflow access cannula 10. More particularly, body 85 of endoscope adapter 15 is designed to seat over stem 60 of cannula mount 50 so that (i) an endoscope 20 can extend down lumen 70 (FIG. 26) of endoscope adapter 15 and down central lumen 40 (FIG. 21) of elongated tube 25, and (ii) fluid introduced through ports 90 of endoscope adapter 15 can flow down to the surgical site through lumen 70 of endoscope adapter 15 and central lumen 40 of elongated tube 25 or, conversely, fluid at the surgical site can flow up through central lumen 40 of elongated tube 25 and lumen 70 of endoscope adapter 15, and then out one of the ports 90. Endoscope adapter 15 also includes keys 80 for mounting in keyways 75 of endoscope adapter 15 when endoscope adapter 15 is connected to, and seats into, inflow access cannula 10. This engagement keeps endoscope adapter 15 connected to inflow access cannula 10 during surgical use.

More particularly, endoscope adapter 15 comprises an annular chamber 95 (FIG. 23) which communicates with a plurality of radial passageways 100, which in turn communicate with an annular opening 105 formed about the perimeter of stem 60. Thus, fluid is able to pass into ports 90, along annular chamber 95, through radial passageways 100, up annular opening 105, down lumen 70 of stem 60 and then down lumen 40 of elongated tube 25. Correspondingly, fluid is able to leave the surgical site by passing up lumen 40 of elongated tube 25, through lumen 70 of stem 60, down annular opening 105, through radial passageways 100, along annular chamber 95 and then out ports 90. In this respect it will be appreciated that an O-ring 106 ensures a fluid seal between body 85 of endoscope adapter 15 and mount 50 of inflow access cannula 10, and an O-ring 107 ensures a fluid seal between body 85 of endoscope adapter 15 and endoscope 20—thus, when endoscope 20 is seated in assembled endoscope adapter 15/inflow access cannula 10, a closed flow path is established between ports 90 and lumen 40 of elongated tube 25. Significantly, O-ring 107 also acts as a spacer to maintain a gap G (FIG. 23) between the proximal end of the endoscope's body B and the mouth of lumen 70 of stem 60, so that fluid can pass from annular opening 105, through gap G and into lumen 70 of stem 60 (or from lumen 70 of stem 60, through gap G and into annular opening 105). Thus it will be seen that with the foregoing construction, ports 90 are disposed distal to the proximal end of stem 60. By virtue of the ports 90 being "below" (i.e., distal) to the top of stem 60, the overall height of the assembled endoscope adapter 15/inflow access cannula 10 is minimized. This provides for a significantly more compact design (in terms of length) which covers a reduced portion of an instrument's length, thereby increasing access of the instrument (e.g., endoscope 20) to deep surgical sites within the joint space. In other words, the compact design of the assembled endoscope adapter 15/inflow access cannula 10 provides a more effective working length to the shaft of endoscope 20 (i.e., the length the endoscope shaft that extends distal to the distal surface of mount 50). Thus, while the flow path between ports 90 and the mouth of lumen 70 of stem 60 may be non-linear with the present invention, a more compact endoscope adapter/inflow access cannula design is obtained and the effective working length of an instrument (e.g., the endoscope) is increased. This is a significant advantage in the art.

Figure 26:
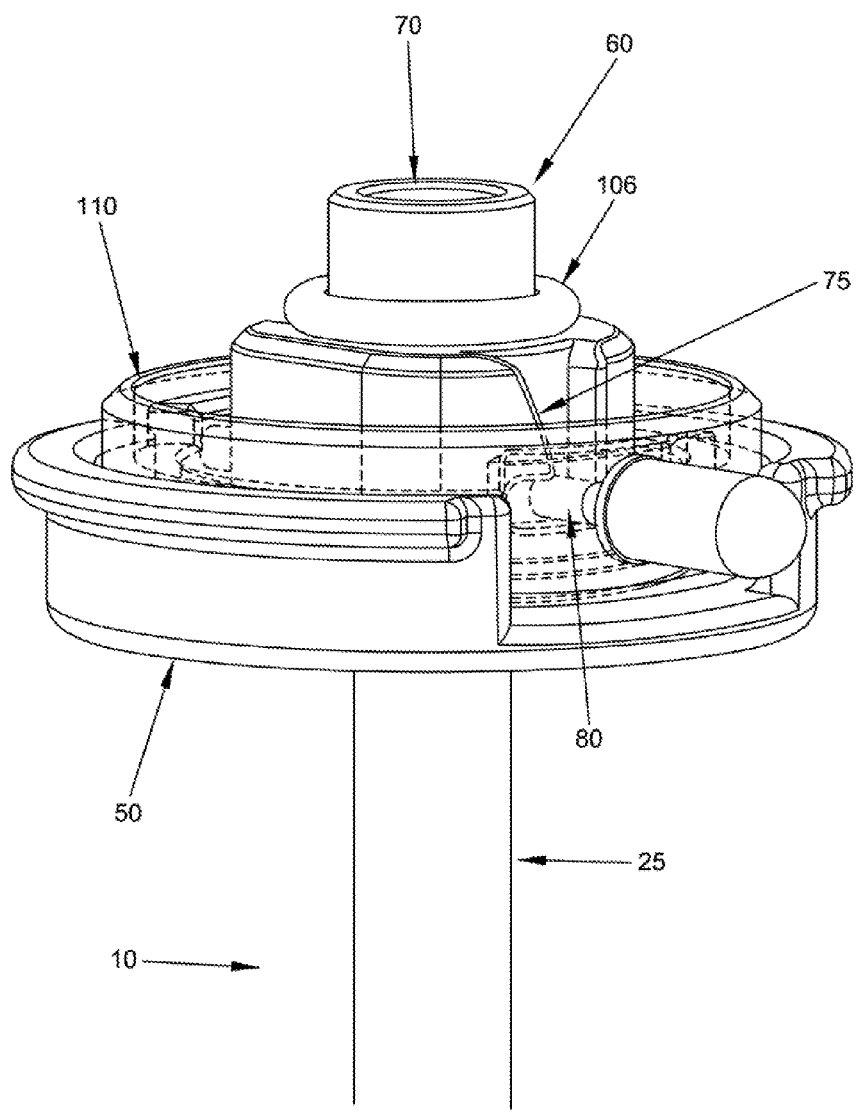
Figure 33:
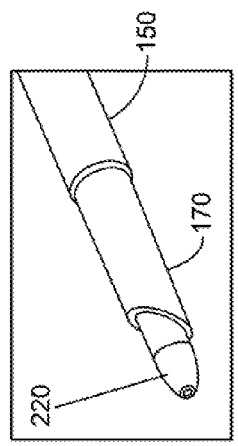

Furthermore, keys 80 are preferably mounted on a rotating collar 110. Rotating collar 110 is rotatably mounted to body 85 of endoscope adapter 15, where it is fixed in the axial direction but can spin about the longitudinal axis of endoscope adapter 15. Rotating collar 110 is spring-biased to force key 80 into the L-shaped keyway 75. As such, when endoscope adaptor 15 is connected to inflow access cannula 10, key 80 will be spring-biased into bottom corner 115 of L-shaped keyway 75. To release, or disengage, endoscope adaptor 15 from inflow access cannula 10, rotating collar 110 is rotated, which shifts key 80 out of bottom corner 115 to the vertical groove portion 120 of L-shaped keyway 75; this enables endoscope adaptor 15 to be moved axially away from inflow access cannula 10. In FIG. 26, rotating collar 110 and straight key 80 (without additional components of endoscope adaptor 15) are illustrated to show engagement of key 80 into the L-shaped keyway 75 of mount 50 of inflow access cannula 10. This design minimizes the length required to connect the endoscope adapter 15 and inflow access cannula 10, hence providing for a more effective working length of the shaft of scope 20.

Inflow access cannula system 5 may be used in various ways to provide access to the interior of a hip joint. Among other things, due to the smooth shaft of elongated tube 25 and the atraumatic distal tip 45 of the elongated tube, atraumatic cannula deployment can be achieved. Furthermore, the use of endoscope adapter 15 allows custom docking (secure seating and fluid flow) to be achieved when an endoscope is mounted in the inflow access cannula. And, significantly, the more compact design (in terms of length) of the assembled endoscope adapter/inflow access cannula covers a reduced portion of an instrument's length, thereby increasing access of the instrument (e.g., endoscope 20) to deep surgical sites within the joint space.

Looking next at FIGS. 27-42, there is shown another inflow access cannula system 125 which generally comprises an inflow access cannula 130, an obturator 135 and an endoscope adapter 140. Obturator 135 is intended to be positioned within an inflow access cannula 130 during insertion of the inflow access cannula into the tissue of the patient, as will hereinafter be discussed in further detail. As will also hereinafter be discussed in further detail, when the inflow access cannula 130 has been properly positioned in the tissue of the patient, obturator 135 is removed, endoscope adapter 140 is positioned on the proximal end of inflow access cannula 130, and an endoscope 145 is advanced through the central lumen of the endoscope adapter and the inflow access cannula, whereby to provide visualization of, and fluid flow to and/or from, a remote surgical site. Alternatively, endoscope adapter 140 may be mounted on endoscope 145 remote from inflow access cannula 130 and then the two elements advanced together as a unit so as to seat on inflow access cannula 130.

More particularly, inflow access cannula 130 generally comprises an elongated tube 150 having a distal end 155, a proximal end 160 and a central lumen 165 (FIG. 41) extending therebetween. The shaft of elongated tube 150 is long enough so that it can extend between the outer surface of the patient's skin and the inside of the joint. Furthermore, the shaft of elongated tube 150 is preferably formed out of metal so as to provide strength and rigidity during insertion of the cannula into the tissue of the patient and its subsequent use as a liner for the access corridor extending down to the remote surgical site. Alternatively, the shaft of elongated tube 150 may be a metal tube coaxial with a plastic tube, the metal tube being disposed either inside or outside of the plastic tube. The outer surface of elongated tube 150 is preferably smooth so as to minimize trauma to tissue as inflow access cannula 130 is inserted in the tissue.

Distal end 155 of inflow access cannula 130 preferably comprises a soft, atraumatic distal tip 170 (FIG. 27) so as to also minimize tissue trauma during cannula insertion and use.

In one preferred form of the invention, at least the atraumatic distal tip 170 of inflow access cannula 130 comprises a polymer or other material which contains barium sulfate, preferably in the range of 5-30% (and preferably about 15%) by weight, so as to render the inflow access cannula visible under X-ray or fluoroscopy. This range (by weight) of barium sulfate is generally preferred since concentrations below 5% tend to be too low for good visualization in hip applications, whereas concentrations above 30% can lead to degradation of material properties. Alternatively, other opacifiers, at appropriate weight concentrations, may also be used to render the inflow access cannula visible under X-ray or fluoroscopy.

A mount 175 (FIG. 27) is secured to the proximal end of elongated tube 150. Mount 175 includes a keyway 180 (FIG. 27) for receiving a key 185 (FIG. 30) of obturator 135, whereby to releasably rotatably lock obturator 135 to inflow access cannula 130. Mount 175 also includes one or more keys 190 (FIG. 37) for receipt in corresponding keyways 195 (FIG. 38) in endoscope adapter 140, whereby to releasably rotatably lock endoscope adapter 140 to inflow access cannula 130. Mount 175 also includes a stem 200 (FIG. 37) which protrudes upward from the floor 205 of mount 175. Stem 200 includes a lumen 210 (FIG. 37) which communicates with central lumen 165 (FIG. 41) of elongated tube 150.

Figure 32:
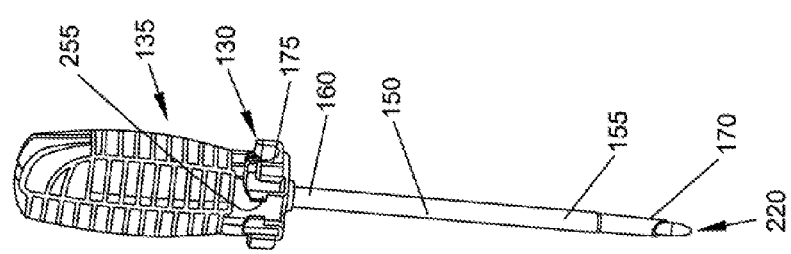
Figure 31:
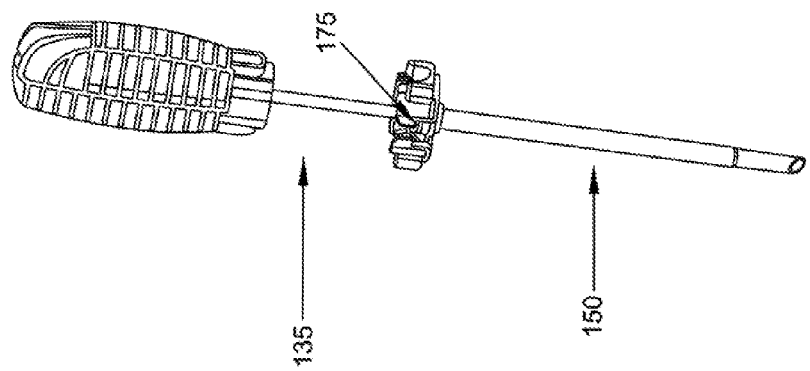
Figure 40:
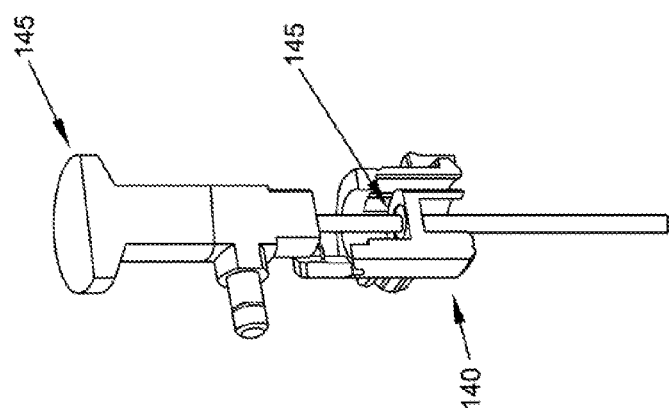
Figure 39:
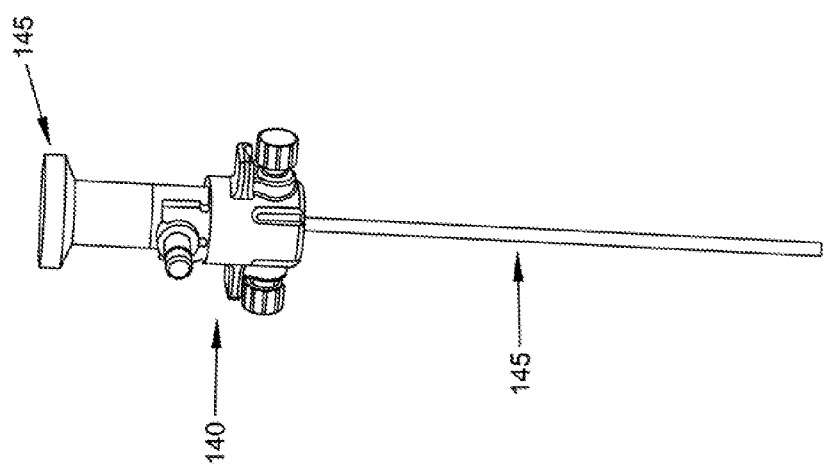
Figure 42:
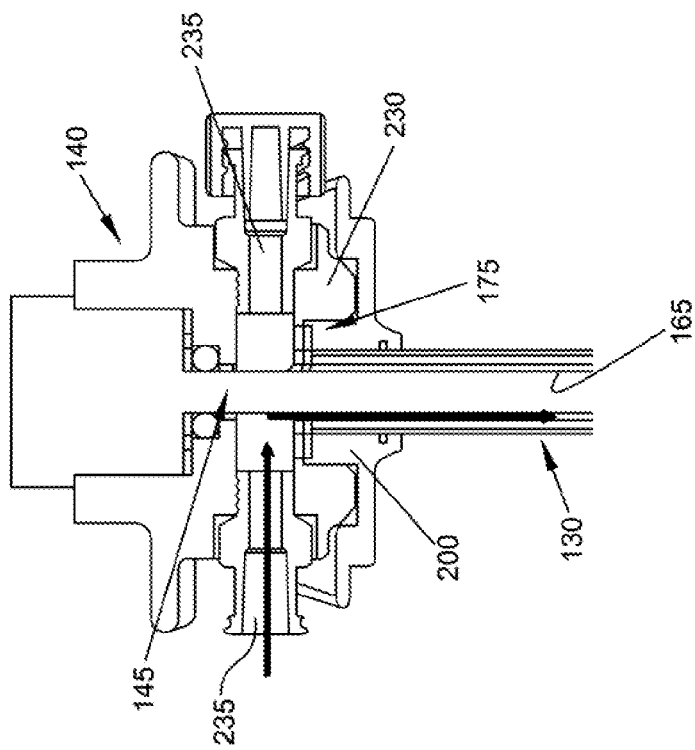
Figure 41:
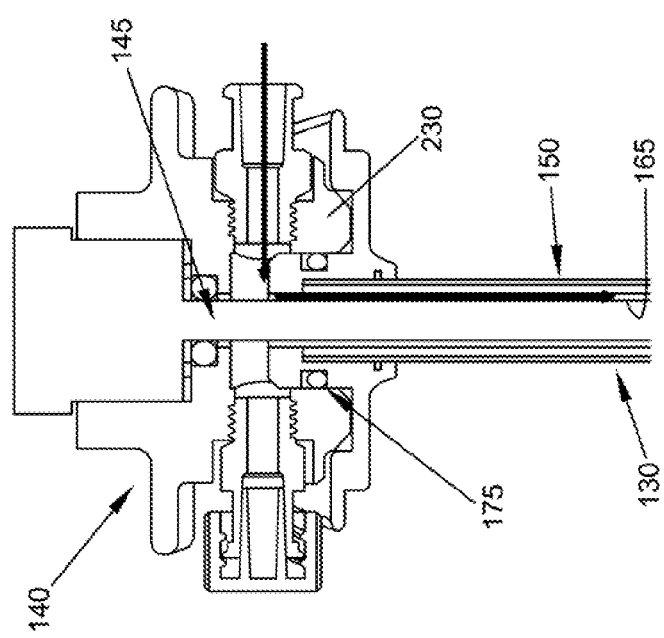

Obturator 135 generally comprises a shaft 215 (FIG. 30) terminating in a blunt distal end 220 and a proximal handle 225. Handle 225 includes a key 185 for receipt in the aforementioned keyway 180 (FIG. 27) of mount 175, whereby to releasably rotatably lock obturator 135 to inflow access cannula 130. As seen in FIG. 32, the distal end 220 of obturator shaft 215 protrudes from atraumatic tip 170 of cannula tube 150 when obturator key 185 is seated in cannula keyway 180, so that the blunt distal end 220 of obturator 135 leads the assembly and prevents tissue coring by inflow access cannula 130 when the inflow access cannula is advanced through tissue.

Endoscope adapter 140 comprises a body 230 (FIG. 41) which mates with mount 175 of inflow access cannula 130. More particularly, body 230 of endoscope adapter 140 is designed to seat over stem 200 of cannula mount 175 so that (i) an endoscope 145 can extend down lumen 210 (FIG. 37) of endoscope adapter 140 and down central lumen 165 of elongated tube 150, and (ii) fluid introduced through ports 235 (FIG. 42) of endoscope adapter 140 can flow down to the surgical site through central lumen 165 of elongated tube 150 or, conversely, fluid at the surgical site can flow up through central lumen 165 of elongated tube 150 and then out one of the ports 235. As noted above, cannula mount 175 also includes keys 190 (FIG. 37) for mating with keyways 195 (FIG. 38) of endoscope adapter 140, so that proper alignment of inflow access cannula 130 and endoscope adapter 140 can be ensured. Cannula mount 175 also includes a keyway 240 (FIG. 27) for mating with flexure key 245 (FIG. 29) of endoscope adapter 140. Flexure key 245 comprises a locking tab 250 which engages notch 255 (FIG. 27) when endoscope adapter 140 is connected to, and seats into, inflow access cannula 130. This engagement keeps endoscope adapter 140 connected to inflow access cannula 130 during surgical use. Flexure key 245 can be compressed and moved radially inwardly (i.e., toward the center axis of endoscope adapter 140) to disengage locking tab 250 from notch 255 and thus allow endoscope adapter 140 to be disconnected from inflow access cannula 130.

Inflow access cannula system 125 may be used in various ways to provide access to the interior of a hip joint. Among other things, due to the smooth shaft of elongated tube 150 and the atraumatic distal tip 170 of the elongated tube, atraumatic cannula deployment can be achieved. Furthermore, the use of endoscope adapter 140 allows custom docking (secure seating and fluid flow) to be achieved when an endoscope is mounted in the inflow access cannula. And, significantly, the more compact design (in terms of length) of the assembled endoscope adapter/inflow access cannula covers a reduced portion of an instrument's length, thereby increasing access of the instrument (e.g., endoscope 20) to deep surgical sites within the joint space.

Use of the Inflow Access Cannula for Other Applications

It should be appreciated that the novel inflow access cannula of the present invention may be used for accessing joints other than the hip joint (e.g., the inflow access cannula may be used to access the interior of a shoulder joint), and/or for accessing other interior body spaces (e.g., the abdominal cavity).

Modifications of the Preferred Embodiments

It should be understood that many additional changes in the details, materials, steps and arrangements of parts, which have been herein described and illustrated in order to explain the nature of the present invention, may be made by those skilled in the art while still remaining within the principles and scope of the invention.

What is claimed is:

1. An inflow access cannula system for allowing an instrument to access a remote surgical site, wherein the instrument comprises a distal portion having a smaller diameter and a proximal portion having a larger diameter, the system comprising:

an inflow access cannula comprising a distal end, a proximal end and a central lumen extending therebetween, wherein the central lumen has a diameter larger than the distal portion of the instrument and smaller than the proximal portion of the instrument; and an instrument adapter for releasable connection to the inflow access cannula, the instrument adapter comprising a lumen communicating with the central lumen of the inflow access cannula, the lumen having a diameter larger than the proximal portion of the instrument, the instrument adapter further comprising a port and a fluid passageway connecting the port with the lumen of the instrument adapter, and a spacer for spacing the proximal portion of the instrument from the distal end of the inflow access cannula, wherein the port is located distal to the proximal end of the inflow access cannula, and further wherein the fluid passageway of the instrument adapter comprises an annular chamber communicating with the port, at least one radially-extending passageway communicating with the annular chamber, and an opening communicating with the lumen of the instrument adapter, such that when an instrument is disposed in the inflow access cannula system so that the distal portion of the instrument extends within the central lumen of the inflow access cannula and the proximal portion of the instrument is disposed in the central lumen of the instrument adapter and is in engagement with the spacer, fluid can flow into the port of the instrument adapter, laterally within the fluid passageway of the instrument adapter, proximally within the fluid passageway of the instrument adapter, laterally within the lumen of the instrument adapter, distally in the lumen of the instrument adapter and distally through the central lumen of the inflow access cannula.

2. A system according to claim 1 wherein the spacer comprises an O-ring.

3. A system according to claim 1 wherein the instrument adapter is releasably mounted to the inflow access cannula by a bayonet mount.

4. A system according to claim 3 wherein the bayonet mount comprises an L-shaped groove formed in the inflow access cannula and a radial pin mounted to the instrument adapter.

5. A system according to claim 4 wherein the instrument adapter comprises a body and a rotating collar rotatably mounted to the body, and wherein the radial pin is mounted to the rotating collar.

6. A system according to claim 5 wherein the rotating collar is spring-biased relative to the body.

7. A system according to claim 1 wherein the inflow access cannula comprises a mount, wherein the mount comprises a stem extending proximally from the mount, and further wherein the stem comprises the proximal end of the inflow access cannula.

8. A system according to claim 7 wherein a seal is disposed between the mount and the instrument adapter.

9. A system according to claim 8 wherein the seal is an O-ring.

10. A system according to claim 9 wherein the O-ring extends coaxially around the stem.

11. A system according to claim 1 wherein the distal end of the inflow access cannula comprises an atraumatic tip.

12. A system according to claim 11 wherein inflow access cannula comprises an elongated tube, and further wherein the atraumatic tip is overmolded around the tube.

13. A system according to claim 1 wherein the instrument comprises an endoscope.

\* \* \* \* \*